US011458194B2

(12) United States Patent
Griscelli et al.

(10) Patent No.: US 11,458,194 B2
(45) Date of Patent: Oct. 4, 2022

(54) METHODS AND COMPOSITIONS FOR TREATING CANCERS

(71) Applicants: INSTITUT NATIONAL DE LA SANTÉ ET DE LA RECHERCHE MÉDICALE (INSERM), Paris (FR); ASSISTANCE PUBLIQUE-HÔPITAUX DE PARIS, Paris (FR); UNIVERSITÉ PARIS-SACLAY, Saint-Aubin (FR); UNIVERSITÉ DE PARIS, Paris (FR)

(72) Inventors: Frank Griscelli, Villejuif (FR); Ali Turhan, France (FR); Annelise Bennaceur Griscelli, Villejuif (FR)

(73) Assignees: INSERM (INSTITUT NATIONAL DE LA SANTE ET DE LA RECHERCHE MEDICALE), Paris (FR); ASSISTANCE PUBLIQUE—HOPITAUX DE PARIS (APHP), Paris (FR); UNIVERSITE PARIS-SACLAY, Saint-Aubin (FR); UNIVERSITE PARIS CITE, Paris (FR)

( * ) Notice: Subject to any disclaimer, the term of this patent is extended or adjusted under 35 U.S.C. 154(b) by 407 days.

(21) Appl. No.: 16/303,705

(22) PCT Filed: May 24, 2017

(86) PCT No.: PCT/EP2017/062604
§ 371 (c)(1),
(2) Date: Nov. 21, 2018

(87) PCT Pub. No.: WO2017/202949
PCT Pub. Date: Nov. 30, 2017

(65) Prior Publication Data
US 2021/0162031 A1 Jun. 3, 2021

(30) Foreign Application Priority Data
May 25, 2016 (EP) .................... 16305607

(51) Int. Cl.
A61K 35/545 (2015.01)
A61K 31/19 (2006.01)
A61K 45/06 (2006.01)
A61K 39/00 (2006.01)
A61P 35/00 (2006.01)

(52) U.S. Cl.
CPC .......... A61K 39/0011 (2013.01); A61K 31/19 (2013.01); A61K 45/06 (2013.01); A61P 35/00 (2018.01); A61K 35/545 (2013.01); A61K 2039/5156 (2013.01); A61K 2039/545 (2013.01); A61K 2039/55511 (2013.01)

(58) Field of Classification Search
None
See application file for complete search history.

(56) References Cited

U.S. PATENT DOCUMENTS

2013/0136722 A1 5/2013 Mahmud
2014/0356949 A1 12/2014 Davis

OTHER PUBLICATIONS

Zhang et al, International Journal of Molecular Medicine; 2013; vol. 31, pp. 147-153.*
Hiroyuki Inoue et al., "Vaccination with irradiated induced pluripotent stem cells genetically engineered to produce GM-CSF confers potent T cells-mediated antitumor immunity," Adoptive Immunotherapy, Poster III, 2013; pp. 1-2.
Androniki Kretsovali et al., "Histone Deacetylase inhibitors in cell pluripotency, differentiation, and reprogramming," Stem Cells International, vol. 2012, Article ID 184154, 2012; pp. 1-11.
Bartlett, David et al., "Oncolytic viruses as therapeutic cancer vaccines", Molecular Cancer, vol. 12, No. 1, Sep. 11, 2013, p. 103.
Bridle, Byram W. et al., "HDAC Inhibition Suppresses Primary Immune Responses, Enhances Secondary Immune Responses, and Abrogates Autoimmunity During Tumor Immunotherapy", Molecular Therapy, vol. 21, No. 4, Apr. 2013, pp. 887-894.
Wei, Dong et al., "Antitumor Effect of Embryonic Stem Cells in a Non-Small Cell Lung Cancer Model: Antitumor Factors and Immune Responses", International Journal of Medical Sciences, vol. 10, No. 10, Jan. 1, 2013, pp. 1314-1320.
Brodie, Set A. et al., "Could valproic acid be an effective anticancer agent? The evidence so far", Expert Review of Anticancer Therapy, vol. 14, No. 10, Oct. 2014, pp. 1097-1100.
Golla, Upendarrao et al., "Investigation of molecular mechanisms of action of Valproic acid, an anticancer drug using budding yeast as a model organism", Yeast, vol. 32, No. Suppl. 1, Sep. 2015, pp. S179-S180.
Debeb, Bisrat G. et al., "Histone Deacetylase Inhibitors Stimulate Dedifferentiation of Human Breast Cancer Cells Through WNT/beta-Catenin Signaling", Stem Cells, vol. 30, No. 11, Nov. 2012, pp. 2366-2377.

(Continued)

Primary Examiner — Bridget E Bunner
Assistant Examiner — Fozia M Hamud
(74) Attorney, Agent, or Firm — Polsinelli PC

(57) ABSTRACT

The inventors have developed a metastatic 4T1 breast tumor model in BALB/c mice. They have shown that the vaccination with xenogeneic embryonic stem cells in combination with valproic acid (VPA) generates a higher anti-tumoral response against breast cancer and inhibits metastasis development. They established that these responses are achieved only by the addition of valproic acid in the therapeutic regimen in comparison to the use ESCs or iPSCs alone. Thus, the inventors provide a new therapeutic strategy to treat cancers expressing embryonic antigens. Accordingly, the present invention relates to i) a population of pluripotent cells and ii) a compound selected from a group which activates MHC expression, as a combined preparation for use in a method for treating a subject suffering from a cancer, comprising a step of administering simultaneously, separately or sequentially to said subject a therapeutically amount thereof.

6 Claims, 12 Drawing Sheets

(56) References Cited

OTHER PUBLICATIONS

Vivian, Jay L. et al., "An allelic series of mutations in Smad2 and Smad4 identified in a genotype-based screen of N-ethyl-N-nitrosourea-mutagenized mouse embryonic stem cells", Proceedings of the National Academy of Sciences of the United States of America, vol. 99, No. 24, Nov. 26, 2002, pp. 15542-15547.

Zheng, Sushuang et al., "Retake the Center Stage—New Development of Rat Genetics", Journal of Genetics and Genomics, vol. 39, No. 6, Jun. 2012, pp. 261-268.

\* cited by examiner (A)

(B)

METHODS AND COMPOSITIONS FOR TREATING CANCERS

FIELD OF THE INVENTION

The present invention is in the field of oncology, and more specifically, the invention relates to an anticancer vaccine combined therapy.

More particularly, the invention relates to methods of producing a composition comprising pluripotent cells presenting multiple neo-antigens and thereof useful in preparing the cancer cell vaccines.

BACKGROUND OF THE INVENTION

The majority of cancers result from random mutations arising during DNA replication in normal stem cells required during development and tissue maintenance. Cancer Stem Cells (CSCs) are heterogeneous and epigenetically plastic in a dynamic status. Tumor cells arising from CSCs are driven by simultaneous accumulation of mutations present on oncogenes, tumor suppressor genes and signaling pathways leading to clonal waves of tumor evolution. In the 'clonal-evolution model' the types of mutations will vary as cancer develops, so that individual cancer cells become increasingly transformed and aggressive. Mutations acquired in early tumor development are sustained in advanced disease.

Changing over time, these mutations lead to oligo-clonal tumor expansion, and cancer cell resistance in association with a progressive immune editing and exhaustion. Mutational signature of cancer is highly associated with genomic instability. Mutations give rise to novel non-self neo-antigens with immunogenic epitope. However, since the tumor microenvironment is generally immunosuppressive, the host immune system is generally not able to properly destroy these cells and fight these cancers. The clinical benefits reported by T cell response with immune checkpoint inhibitors is well correlated with the mutation rate and mutation landscape of the tumors.

Cancer stem cells (CSCs) represent a minor population of self-renewing cancer cells that contribute to tumor persistence and recurrence since they are frequently resistant to conventional treatments. CSCs initially discovered in hematopoietic malignancies were described in solid tumors from various origins including beast, glioblastoma, prostate, colon head and neck squamous cell carcinoma, ovarian bladder, lung, pancreatic cancer. CSCs have the characteristic of forming xenograph tumors in mice and tumor initiation capacity. In addition, they are radio- and chemo-resistant, contributing to lack of therapeutic response in patients. CSCs persistence thereby causes tumor relapse and/or metastasis following the completion of therapy. Several publications have shown a molecular link between tumor pathogenesis and the Embryonic Stem Cell (ESC) state. CSC express a large number of embryonic antigens that are also expressed by human Embryonic Stem Cells (hESCs) and human Induced Pluripotent Stem Cells (hiPSCs).

Primarily OCT4, NANOG, and SOX2 transcription factors are master regulators and work together as part of a highly integrated network (related to c-myc and polycomb network) to drive the transition from a somatic cell to either a CSC or iPSC by using epigenetic machinery to remodel the chromatin through histone modification and DNA methylation. These factors are absent in normal adult stem cells. Embryonic stem cell-like gene expression and under-expression of Polycomb-regulated genes defining human pluripotent stem cell (ESC/IPSC) identity are associated in poorly differentiated human tumors with poor clinical outcome and distant recurrence after chemo-radiotherapy whatever the origin of cancers (breast, pancreas, bladder, lung, prostate, medulloblastoma.). Poorly differentiated tumors with a "sternness" profile are related to mesenchymal traits on carcinoma cells with epithelial-mesenchymal "EMT" markers, low levels of MHC-I expression, immunosuppressive tumor microenvironment with pro-tumoral inflammatory leukocytes, stromal cells and macrophages. Tumor cells undergoing EMT acquire sternness properties and become CSC with the capacity to migrate very early throughout the organism and to persist in a dormant stage for long periods of time. CSCs act as a reservoir to seed and replenish the tumor compartment. They also expand by self-renewal, disseminating to different tissues, generating metastases. These CSCs share pluripotent embryonic gene signatures and are resistant to anti-cancer drugs and radiotherapy. They also escape immune anti-tumor defenses for the reasons indicated above (immune-depressive micro-environment).

It was reported that foetal tissues can be used to immunize mice and that this can induce the rejection of transplanted tumors, including cancer of the skin, liver, and gastrointestinal tract. This response has been explained by the fact that those tumor cells express a high number of oncofetal antigens.

To date several human cancer vaccine trials have been set up in order to target embryonic antigens such as carcinoembryonic antigen (CEA), alpha fetoprotein or cancer/testes antigens. Unfortunately, targeting one antigen alone was shown to be not efficient enough to generate strong antitumor immune responses to mediate tumor rejection because of rapid appearance of escape mutants leading to the general inefficiency of monovalent cancer vaccines.

Recent interest in the potential of stem cells in regenerative medicine has made well-defined ESC lines widely available as well as iPSCs that are phenotypically and functionally similar to ESCs.

Cancer-associated epigenetic aberrations are a characteristic trait of cancer stem cells involving every component of epigenetic machinery (DNA methylation, histone modifications, non-coding RNAs, specifically microRNA expression).

Several epigenetic modifying drugs with tumor-inhibiting activities, are currently in clinical use in oncology, including hypomethylating agents such as azacitidine or decitabine and histone deacetylase inhibitors such as vorinostat or romidepsin.

Using such drugs, it was possible to reprogram cancer cells. In addition, epigenetic reprogramming of the tumor micro-environment by epigenetic drugs is an attractive manipulating approach of cancer therapy as there is clear evidence of cancer-stroma interaction in cancer development.

Thus, there continues to be a need for new approaches to prevent and/or treat cancers having stem cells signature. These cancers express a set of embryonic genes (i.e also called neo-antigens) in common with ESC/IPSC, and include, in particular, pancreatic cancer, breast cancer, ovarian, colon cancer, lung kidney, prostate carcinomas, medulloblastoma, cholangiocarcinoma, liver cancer, chronic and acute leukemias and myeloma. This class of cancer is mostly associated with a mesenchymal like-signature which needs to develop therapies targeting specifically the CSCs for improving survival and enhancing quality of life of cancer patients. In particular such strategies should lead to the restoration of a permissive anti-tumor micro-environment (the tumor micro-environment is generally immunosuppressive and thus should be remade immuno-competent) combined with an immune anti-CSC response. This and other needs are addressed in whole or in part by the presently disclosed subject matter.

SUMMARY OF THE INVENTION

The present invention is based on the determination, by the inventors, that HDACi (Histone deacetylase inhibitors) can be used to stimulate an immune response in a patient, against an antigen of interest, when an immunogenic composition, containing said antigen of interest, or targeting said antigen of interest, is administered to the patient, in combination with an HDACi, optionally followed by a further treatment with an HDACi. The immunogenic composition is intended to allow the onset of an immune response against (an) antigen(s) of interest. The use of HDACi as an adjuvant is particularly interesting for treatment of cancers, in particular for cancers having stem cell signature. The present invention is defined in particular by the claims.

DETAILED DESCRIPTION OF THE INVENTION

Figure 1:
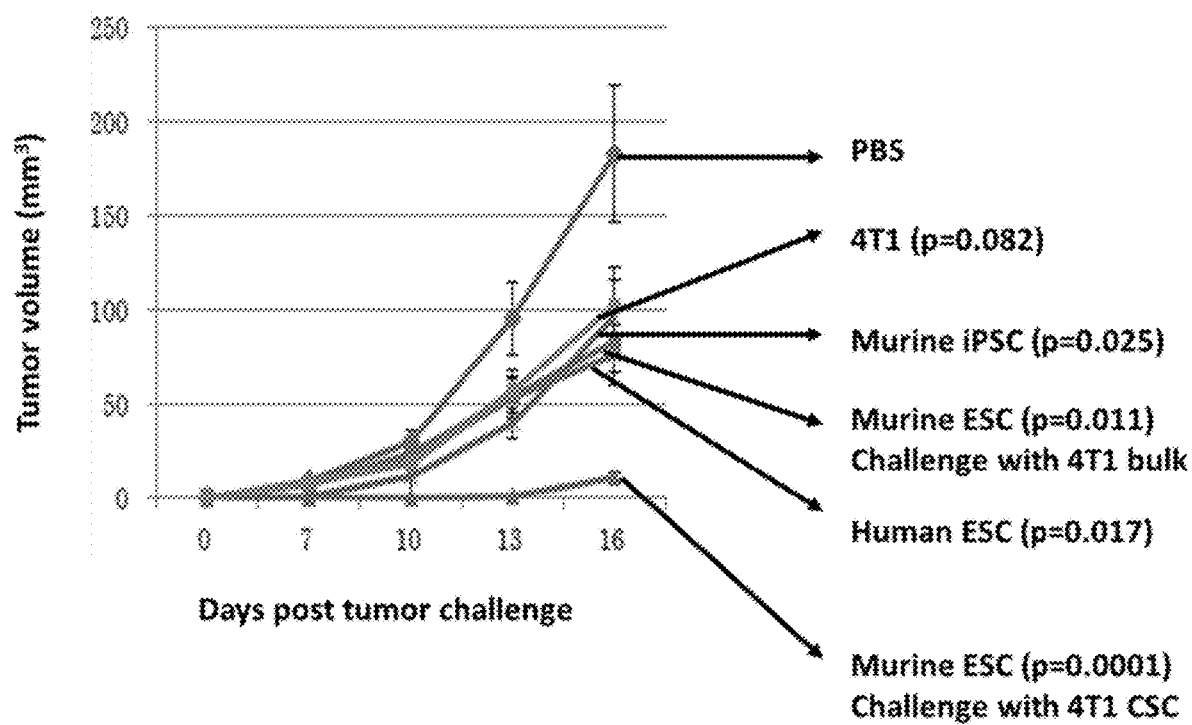
FIG. 1: Vaccination study with mESCs, hESC, miPSCs and 4T1 cells on breast tumor 4T1 model. Study design: Mice (n=5 per group) received to boosts of vaccine 7 and 14 days with $10^5$ irradiated cells; murine Embryonic Stem Cells (mESCs), murine induced Pluripotent Stem Cells (miPSCs), human Embryonic Stem Cells (hESCs) or 4T1 cells. After 14 days $5\times10^4$ 4T1 cells were injected into the mammary fat pad of the mice. Fiver mice were injected with 4T1-CSC (4T1 cells growth with additional cytokines such as TGF-beta and TNFalpha in order to generate CSC growing in the form of mammospheres)

The inventors have shown that use of an HDACi together with a population of pluripotent cells led to a synergy and an efficient response of the immune system against tumor cells.

Indeed, the inventors further hypothesized that pluripotent stem cells such as hESCs or hiPSCs could be used as a vaccine to generate an immune response against a variety of embryonic antigens that are shared by tumor cells. They found, that the vaccination of mice with hESCs or hiPSCs in combination with a compound that is able to induce MHC I, such as valproic acid was able to induce efficient immune and anti-tumoral responses against breast carcinoma without evidence of side effects and autoimmune diseases. In addition they found that this combined regimen was associated with a significant inhibition of lung metastasis. Surprisingly, they established that these responses are greatly improved by the addition of HDACI, and in particular valproic acid in the therapeutic regimen in comparison to the use of ESCs or iPSCs alone.

HDACi for Improving Immune Response

The invention relates to a method for increasing efficacy, in a patient, of a vaccine composition, comprising the step of administering an HDACi to the patient together with the vaccine composition. In particular, the HDACi can be added to the vaccine composition.

Increased efficacy can be understood as increasing immunogenicity of the vaccine composition, increasing the immune response against the vaccine composition, or increasing the immune response generated by the vaccine composition. This can be compared to the immune response generated in the absence of HDACi.

The vaccine composition contains an immunogenic element intended to make the patient develop an immune response against one or more antigen(s) of interest. An antigen of interest are any antigen against which an immune response is desired, and include any peptide, protein either from the self (such as antigens from cancer cells) or exogenous such as bacterial, viral, or parasitic protein, other kind of antigens such as nucleic acids, sugars, lipopolysaccharides and the like.

The invention thus relates to the use of a HDACi as an adjuvant, in particular for increasing the immune response against a vaccine composition, as well as to HDACi for its use as an adjuvant, or for increasing the immune response against a vaccine composition. The invention also relates to the use of an HDACi for the manufacture of a vaccine composition containing one or more antigen(s) of interest, intended to have the patient develop an immune response against the antigen(s) of interest.

The method and use herein disclosed are particularly interesting when the vaccine composition is a cancer vaccine composition, i.e. contains antigen(s) of interest that are expressed by cancer cells. In particular, the method and use are very adapted for solid tumor cancers. Indeed, in these types of cancers, the immune micro-environment is particularly immunosuppressive (i.e. there are an expression of cytokines and of molecular signals, and recruitment of such CD4 cells, that the potency of immune cells against the cancer antigens is decreased); without being bound by this theory, it is postulated the presence of the HDACi will modify the micro-environment and allow the immune cells to be potentiated to fight the cancer cells, probably by modifying expression of the genes that have an immunosuppressive effect in the cells that are present in, near or around the tumor.

The method herein described may also comprise the step of administering an HDACi for a few days after the administration of the vaccine composition. This continuous administration of an HDACi can be useful for maintaining the microenvironment modification for a time long enough for the immune cells to be able to "take over" the tumor.

Generally, this further continuous administration of the HDACi will consist in a daily administration of an adequate dose of the HDACi, for at least three days following vaccine administration, and up to one month. It is, however preferred when the further HDACi administration is performed for at least one week, more preferably at least or about two weeks.

The vaccine composition contains an immunogenic element (compound) intended to make the patient develop an immune response against one or more antigen(s) of interest.

This immunogenic element may be an antigen (or multiple antigens). This antigen can be, as seen above, of any form, depending on the target cells (which is intended to include host cells, as well as bacterial cells, parasitic pathogens or viral particles). It can also be formulated with any adjuvant (immune-stimulant) known in the art such as alum or Freund's complete or incomplete adjuvants.

In another embodiment, the immunogenic compound is an extract from a cell composition, wherein cells of said composition express an antigen of interest. The cellular extract may be lysed cells that have been centrifuged to remove insoluble matter such as membrane fragments, vesicles, and nuclei, and thus consist mostly of cytosol. In another embodiment, the extract may have been made using specific techniques to deplete or enrich specific components (for example sonication can be used to break large membrane fragments into small particles that remain in the extract, or high speed centrifugation to remove the smallest insoluble components). The cell extract is obtained by any chemical or mechanical action, such as by pressure, distillation, evaporation and the like.

In another embodiment the immunogenic element is a cell composition, wherein cells of said composition express the antigen of interest. In this embodiment, it is preferred when the membrane of the cells is preserved (so that presentation of the antigen is made through the MHC-I pathway). It is preferred when the cells are inactivated, as described below.

In these embodiments, the cells may be pluripotent cells, as described below, cancer cells, virus-infected cells or bacterial cells.

In another embodiment the immunogenic element is a cell composition comprising Antigen-Presenting-Cells (APCs) that have been primed in vitro by antigens of interest. This composition is an antigen-presenting cell vaccine, made of antigens and antigen-presenting cells (APCs). Antigen-presenting cells are cells that display antigen complexed with major histocompatibility complexes (MHCs) on their surfaces. One can cite dendritic cells (DC), which are preferred in the context of the invention, as they are able to present antigen to both helper and cytotoxic T cells, macrophages, or B cells. These APCs may be natural cells, or engineered cells. One can, in particular, cite Eggermont et al (Trends in Biotechnology, 2014, 32, 9, 456-465) which review advances in developing artificial antigen-presenting cells. Methods of developing anti-cancer vaccines, using APCs, have been widely proposed in the art and are known by the person skilled in the art.

In another embodiment, the immunogenic element does not actually contain an antigen, but consists in a composition of T cell lymphocytes that have been primed in vitro against the antigen of interest, for instance by exposure to Antigen-Presenting-Cells presenting the antigen of interest. Consequently, this composition is able to onset an immune response in vivo against the antigen of interest. This strategy can be called "adoptive transfer of T cells", and it is known that such adoptively transferred T cells persist for long periods of time in vivo and readily migrate between the lymphoid and vascular compartments (Bear et al, J Biomed Biotechnol. 2011; 2011:417403; Melief et al, J Clin Invest. 2015; 125(9):3401-3412).

In all these embodiments, an HDACi is administered in combination with the vaccine composition containing the immunogenic element. Said administration may be simultaneous, separate or sequential, as disclosed below for the embodiment where the immunogenic element is a composition of pluripotent cells. It is to be noted that all descriptions below, that are disclosed for the composition of pluripotent cells are equally applicable to the vaccines comprising any immunogenic element as disclosed above.

The present specification emphasizes an HDAC inhibitor (in particular valproic acid), together with a composition of pluripotent cells, as such pluripotent cells express neoantigens that are also found in very aggressive cancers, as reminded above. Consequently, whatever the immunogenic element, it is preferred when the antigen of interest is a neo-antigen that is expressed by cancer cells, as described above and also below.

In particular, the immunogenic element is a cell composition, wherein the cell composition has been obtained by expansion and inactivation of pluripotent cells, as further disclosed in details below.

Method of Treating a Subject Suffering from a Cancer with a Combined Preparation The present invention relates a method of treating a subject suffering from a cancer comprising a step of administration simultaneously, separately or sequentially to said subject a therapeutically amount of i) a population of pluripotent cells and ii) a compound selected from a group which activates MHC expression and/or immune response, as a combined preparation.

In the preferred environment, the cells have been cultured so as to present neo-antigens through the MHC I pathway and, in particular, some cells of the population present mutated. The compound used in combination with the cells may also preserve pluripotency of the cells. It is greatly preferred when the administration of the cells is followed by administration of a compound which activates MHC expression and/or immune response (preferably the same than the one that has been initially administered in combination, but potentially another one) to enhance immune response.

As used herein, the terms "treating" or "treatment" refer to both prophylactic or preventive treatment as well as curative or disease modifying treatment, including treatment of subject at high predisposed risk of contracting cancer such as hereditary family cancer syndromes or suspected to have contracted a cancer as well as subject who are ill or have been diagnosed as suffering from a cancer or medical condition, and includes suppression of clinical relapse. The treatment may be administered to a subject having a cancer or who ultimately may acquire the cancer, in order to prevent, cure, delay the onset of, reduce the severity of, or ameliorate one or more symptoms of cancer or recurring cancer, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, (e.g., weekly, monthly, yearly, etc.) or intermittent therapy (e.g., interrupted treatment, intermittent treatment, treatment at relapse, or treatment upon achievement of a particular predetermined criteria (e.g., pain, disease manifestation, etc.).

As used herein, the term "administration simultaneously" refers to administration of 2 active ingredients by the same route and at the same time or at substantially the same time. The term "administration separately" refers to an administration of 2 active ingredients at the same time or at substantially the same time by different routes. The term "administration sequentially" refers to an administration of 2 active ingredients at different times, the administration route being identical or different.

As used herein, the term "subject" refers to any mammals, such as a rodent, a feline, a canine, and a non-human and human primate. Particularly, in the present invention, the subject is a human afflicted with or susceptible to be afflicted with cancers which having an expression of pluripotent embryonic-like stem cell antigens.

As used herein, the term "population" refers to a population of cells, wherein the majority (e.g., at least about 20%, preferably at least about 50%, more preferably at least about 70%, and even more preferably at least about 80%, and even more preferentially at least about 90%) of the total number of cells have the specified characteristics of the cells of interest (e.g. pluripotency markers for iPSC, ESC defined by international stem cell initiative including at least 96 markers (Adewumi et al, Nat Biotech 2007), and gene-expression based assay (PluriTest) (FJ Muller, Nature Methods 2011).

Particularly, the term "a population of pluripotent cells" refers to a population of cells where the characteristics of the cells is expression of the pluripotency markers for iPSC, or ESC. These cells are preferably selected from the group consisting of human embryonic stem cells (hESC), induced human pluripotent stem cells (hiPSC), allogeneic, xenogeneic or syngeneic/autologous stem cells.

As used herein, the term "pluripotent" refers to cells with the ability to give rise to progeny that can undergo differentiation, under appropriate conditions, into all cell types derived from the three germ layers (endoderm, mesoderm, and ectoderm) with specific cell lineages characteristics. The term "pluripotent" includes normal embryonic stem cells (ESCs), or very small embryonic-like stem cells (VSELs) or engineered induced pluripotent stem cells (iPSCs), reprogrammed from all sources and cell origins of adult somatic cells (ASCs).

Pluripotent stem cells contribute to tissues of a prenatal, postnatal or adult organism. Standard art-accepted tests are used to establish the pluripotency of a cell population such as the ability to form a teratoma in 8-12 week old SCID mice, and various pluripotent stem cell characteristics. More specifically, human pluripotent stem cells express at least some (at least three, more generally at least four or five), and optionally all, of the markers from the following non-limiting list: SSEA-3, SSEA-4, TRA-1-60, TRA-1-81, TRA-2-49/6E, Alkaline phosphatase (ALP), Sox2, E-cadherin, UTF-I, Oct4, Lin28, Rex1, Nanog, TERC, TERT.

Pluripotent stem cells traditionally arise from the blastocyst stage of embryonic development and have the ability to develop into all types of fetal and adult cells except perhaps for placenta. Embryonic pluripotent stem cells (ESC) generally can be isolated from a 50- to 150-cell, 4- to 5-day-old post-fertilization blastocyst. While ESCs are capable of indefinite ex vivo proliferation, they exist only transiently in vivo during embryogenesis. Various animal (including human) ESC lines, such as, for example, NIH approved cell line WAO9 human ESCs can be obtained commercially from WiCell Research Institute, Madison, Wis. Human ESC lines, such as Cecol-14, can be obtained commercially for example from Cecolfes, Bogota, Colombia. Of course, other embryonic stem cell lines may be used, if desired.

As used herein, the term "Embryonic stem cell" refers to pluripotent cells of humans (i.e., hESC). The hESC are isolated from a pre-blastocyst stage embryo. In another embodiment, the hES cells are prepared by dedifferentiation of at least partially differentiated cells (e.g., multipotent cells) and are totipotent in practice. Methods of preparing hESC are well known and taught, for example, in U.S. Pat. Nos. 5,843,780, 6,200,806, 7,029,913, 5,453,357, 5,690, 926, 6,642,048, 6,800,480, 5,166,065, 6,090,622, 6,562,619, 6,921,632, and 5,914,268, U.S. Published Application No. 2005/0176707, International Application No. WO2001085917. In the context of the invention, the human embryonic stem cell (hESC) are generated without embryo destruction according to the technology as described in Chung et al 2008.

As used herein, the term "induced pluripotent stem cell" refers to a pluripotent stem cell artificially derived from a non-pluripotent cell by a reprogramming procedure, using methods known in the art and initially disclosed by Yamanaka (in particular WO2012/060473, PCT/JP2006/ 324881, PCT/JP02/05350, U.S. Pat. Nos. 9,499,797, 9,637, 732, 8,158,766, 8,129,187, 8,058,065, 8,278,104. In short, somatic cells are reprogrammed to induced pluripotent stem cells (iPSCs) by ectopic expression of defined factors such as Oct4, Sox2, Klf4 and c-My, or Oct4, Sox2, Lin28 and Nanog. In a particular embodiment, the induced pluripotent stem cells are derived from mammals in particular (but not limited to) rodents, pigs, cats, dogs, and non-human primates, and human.

iPSCs have been successfully generated from somatic cells of various origins (fibroblast, blood cells, keratinocytes . . . ) and by using variable technologies (such as integrative lentivirus/retrovirus and non integrative vectors such as sendaï of virus, episomal vectors, synthetic mRNA, Adenovirus, rAAV, recombinant proteins . . . ) with or without small chemical compounds.

Small molecules can be used to enhance induction and quality of mouse and human iPSCs by acting as epigenetic modifiers (i.e. modifying expression of some genes). As an illustration, one can cite BIX01294 (BIX, a G9a histone methyltransferase inhibitor), sodium butyrate (NaB, an histone deacetylase HDAC inhibitor) or S-adeno-sylhomocysteine (SAH, a DNA demethylation agent), 5-azacytidine (5-AZA, a DNA methyltransferase inhibitor), Valproic acid (VPA, another histone deacetylase inhibitors) also improves reprogramming and quality of normal iPSCs.

Fully reprogramed bona-fide iPSC express similarly pluripotent genes than embryonic stem cells with self-renewal capacity and represent an unlimited stem cell (or stem cell like) resource.

ESC and IPSC can be amplified iteratively during multiple and illimited passages allowing scalable stem cells resources. Pluripotency potential is actively maintained in permissive culture conditions, by preserving high level expression of pluripotency genes. These methods are known in the art.

Specific culture conditions and methods allow to replicate a stable genome, but some exome mutations and epigenomic modifications have nevertheless been described (Gore A and al. Nature 2011).

As used herein, the term "somatic cell" refers to any cell of the body except germline cells (sperm and egg).

As used herein, the term "allogeneic cells" refers cells from the same species but genetically distinct.

As used herein, the term "syngeneic or autologous cells" refers to cells from the same species and the same genetic background.

As used herein, the term "xenogeneic cells" refers to cells from different species and genetically distinct.

In a particular embodiment, the stem cells can be derived from mammals but not limited to rodents, pigs, cats, dogs, and primates, including humans.

Method for Producing a Population of Pluripotent Cells

In a first aspect, the invention relates to a method for producing a cell composition, comprising the steps of
i) expanding pluripotent cells, in the presence of such conditions as to maintain the pluripotent ability of the cells, in the presence of an agent that induces MHC-I presentation of antigens in said population during the expansion step
ii) Exposing the expanded cells to an inactivating agent that will inactivate the cells,
iii) Recovering and conditioning the expanded inactivated cells.

In a specific embodiment the cell envelope integrity is maintained in step ii).

In another embodiment, the cells are inactivated and a cell derived product is obtained, such as cell extracts.

The cell composition produced according to the method above can be used for cancer treatment, according to the methods disclosed herein.

Agent for MHC I Antigen Presentation

Pluripotent cells are expanded in the presence of an agent that will improve the presentation of antigens through the MHC I pathway. Such improved expression can be checked by comparing the number of MHC I molecules at the surface of the cells in the presence or in the absence of the agent. Such agents are known in the art and one can cite, in particular histone deacetylase inhibitors (HDACis). Numerous products having this activity are known in the art, among these HDACis, one can cite, in particular valproate (VPA or valproic acid, CAS number 99-66-1). Other HDACis that can be used (as they have the same mode of action than VPA) are, in particular, vorinostat, romidepsin chidamide, panobinostat, belinostat, panobinostat, mocetinostat, abexinostat, entinostat, SB939, resminostat, givinostat or quisinostat. These agents are present in the cell culture (expansion) medium during the expansion of the pluripotent cells.

Maintaining the Pluripotency of the Cells

Expansion of the cells is performed in conditions so as to maintain the pluripotent ability of the cells (medium, temperature). These culture conditions are known in the art. Maintenance of the pluripotent ability of the cells will ensure that such cells will express (and hence present) all embryonic antigens, thereby increasing the capability of the cells of presenting such antigen at their surface through the MHC I pathway.

The more embryonic antigens presented on the pluripotent cells surface, the increased probability that at least one of these antigens will also be present at the surface of the cancer cells, which will then be recognized and targeted by the immune system that will have been primed by the vaccine composition of the invention.

Hence, maintenance of the pluripotency of the cells of the composition according to the invention, obtained by the methods herein disclosed, leads to presentation of a wide variety of embryonic antigens, and thus to the ubiquitous potency of the vaccine composition of the invention in the treatment methods herein disclosed.

Expansion of the cells in conditions such as to maintain pluripotency is known in the art. It is described, in particular, in all iPSC expansion protocols described to date (Shi Y and al, Nat Rev Drug Discovery 2017; Chen KG and al Cell Stem Cell. 2014). It is preferred when the following conditions are used:
- Use of E8 medium or all clinical grade ES/iPSC culture medium, optionally supplemented with VPA and/or mutagen agents (such as ENU, see below).
- Temperature of 37° C. with or without hypoxia conditions
- Change of the medium every day using the same medium with addition of VPA (from 0.1 mM to 5 mM) and/or ENU (0.1 µg/ml to 100 µg/ml) and/or p53 inhibitor and/or compound that enhance cell survival such as Y-27632 Rock inhibitor.

The cells are generally cultured for 8 weeks, with an optimal density of 90% maintained by regular passages once a week using enzymatic detachment (collagenase, trypsine).

Inactivating the Cells

In the preferred embodiment, the pluripotent cells that are used in the method of treatment herein disclosed are inactivated. The term "inactivated", and grammatical variants thereof, is used herein to refer to a cell (e.g., a pluripotent cell) that is alive but has been rendered incapable of proliferation (i.e., mitotically inactivated). The skilled in the art may use techniques that are known in the art including, but not limited to exposure to chemical agents, irradiation and/or lyophilization. Pluripotent cells can be inactivated such that upon administration to a subject the pluripotent cells are incapable of dividing and thus cannot form teratomas in the subject. It is understood that in the context of a plurality of cells, not every cell needs to be incapable of proliferation. Thus, as used herein the phrase "inactivated to an extent sufficient to prevent teratoma formation in the subject" refers to a degree of inactivation in the population as a whole such that after administration to a subject, a teratoma does not form since the irradiated pluripotent stem cells did not divide anymore as confirmed by in vitro culture. It is to be noted that, even if a one or more cells in the plurality of cells are in fact capable of proliferation in the subject, it is postulated that the immune system of the host will destroy those cells before a teratoma could form. Such inability of proliferation and teratoma formation may be confirmed by testing in mice having a functional and a non-functional immune system.

In some embodiments, an "inactivated" cell is a killed cell, and in some embodiments, the inactivated cell is a whole cellular lysate, pluripotent stem cells derived exosomes, enriched cancer stem neo-antigens, a whole purified cancer stem neo-antigens, DNA RNA and protein extracts, a whole cells suspension that has been lyophilized, a fraction of a cellular lysate such as a membrane fraction, a cytoplasmic fraction, or a combination thereof. Inactivated pluripotent stem cells remain capable of stimulating immune response when the vaccination of mice is carried out with hESCs or hiPSCs in combination with valproic acid or another HDACi. This vaccination is able to induce efficient immune and anti-tumoral responses against 4T1 breast carcinoma without evidence of side effects and autoimmune diseases.

Typically, to inactivate the stem cells, they can be exposed to lethal doses of radiation, (e.g., 5 to 100 Gy single fraction). The precise radiation dose delivered to the cells and length of dose are not critical so long as the cells are rendered nonviable.

Recovering and Conditioning the Cells

The recovery step of the method includes one (or multiple) step(s) of washing the cell culture and resuspending the cells in any appropriate medium such as X-Vivo/Stemflex media or any other clinical grade cell media.

The conditioning of the cells may include freezing or lyophilizing the cells, in order to be able to store the cell composition before use.

Mutating the Pluripotent Cells and Expressing Neo-Antigens

It is reminded that pluripotent cells are cells that are genetically very stable. Indeed, since they are present very early in the process of embryo development and they must multiply for embryo development, it is important that these cells are not too prone to mutations in order to have homogeneity in the embryo.

Consequently cells present in a population of pluripotent cells are generally very homogenous when considering their genetic content (i.e. more than 95% of the cells of the population present the same genetic background.

When preparing iPSCs, a selective advantage of some cells occur during multiple passages, which leads to the population of iPSCs clones that present particular mutations at late passages, but the sequence of the cell genomes are similar close to 100%.

However, after several passages, iPSC are as stable as hESC (Hussein SM and al, Nature 2011). Culture-induced (adaptive) mutations will be acquired with a very few genetic changes upon prolonged culture (Hussein SM and al, Bioessays, 2012).

It is however, favorable to be able to induce mutations in the cells in order to increase the variability of the fetal/embryonic neo-antigens on the treated cellular material that are found in the aggressive cancers. In this way it will increase the possibility for the immune system to generate T cells against these mutated cells and be able to fight cancer cells as well as those that would undergo later variation during growth of the tumor.

This would help to fight the cancer that results from accumulation of genetic alterations resulting from DNA replication errors and/or environmental insults during proliferation of cancer stem cells. These alterations include cancer driver mutations that initiate carcinogenesis and genome destabilizing mutations. This increased genome instability results in clonal evolution leading to the selection of more aggressive clones with increased drug resistance.

Consequently, in a specific embodiment, the cells are expanded in conditions that will induce mutations in genes of said cells.

The cells can thus be exposed to a mutagenic agent, i.e. a physical or chemical agent that changes the genetic material, usually DNA, of an organism and thus increases the frequency of mutations above the natural background level.

The mutagen can be selected from the group consisting of physical mutagens and chemical mutagens.

Among physical mutagens, one can cite
- ionizing radiations such as X-rays, gamma rays and alpha particles which may cause
- DNA breakage and other damages. One can, in particular cite radiations from cobalt-60 and cesium-137. The level of irradiating rays shall be much lower the one that is used for cells inactivation and can be designed by the person skilled in the art
- ultraviolet radiations with wavelength above 260 nm, which can cause error in replication if left uncorrected.
- or radioactive decay, such as 14C in DNA.

Among chemical mutagens, one can cite
- Reactive oxygen species (ROS), such as superoxide, hydroxyl radicals, hydrogen peroxide.
- Deaminating agents, such as nitrous acid which can cause transition mutations by converting cytosine to uracil.
- Polycyclic aromatic hydrocarbon (PAH), which can bind to DNA when activated to diol-epoxides.
- Alkylating agents such as ethylnitrosourea (ENU, CAS number 759-73-9), mustard gas or vinyl chloride.
- Aromatic amines and amides such as 2-Acetylaminofluorene
- Alkaloid from plants, such as those from *Vinca* species
- Bromine and some compounds that contain bromine
- Sodium azide
- Bleomycin
- Psoralen combined with ultraviolet radiation
- Benzene
- Base analogs, which can substitute for DNA bases during replication and cause transition mutations
- Intercalating agents, such as ethidium bromide, proflavine, daunorubicin
- Metals, such as arsenic, cadmium, chromium, nickel and their compounds which may be mutagenic In this embodiment, one will obtain a population of pluripotent stem cells in which the cells have random mutations (generally different from cell to cell, thereby leading to a heterogeneous population), in particular in cancer related neo-antigens.

The inventors have shown that it is possible to design culture conditions that make it possible to induce DNA replication errors in pluripotent stem cells without triggering DNA damage-dependent apoptosis.

This is particularly surprising as, as indicated above, pluripotent cells are naturally very stable for there should be as low number as possible mutations introduced during the early stages of embryogenesis. It results from this that the DNA repair machinery is very efficient in these cells, thereby correcting most defects and/or inducing apoptosis in case it is not possible to correct these defects.

In one embodiment, pluripotent cells (such as ESCs or IPSCs) of a starting population are expanded and maintained in pluripotent permissive culture media (as known in the art) to preserve the pluripotent stage during iterative passages. In these conditions, one would generally observe a low amount of exome mutations (5-10 mutations per exome).

The pluripotent cells are then cultured in vitro with mutagenesis compounds methods to induce and increase genomic instability within the pluripotent stem cells, such as the ones listed above. DNA damage is well confirmed by phosphorylation of γH2AX as a marker for Double-Strand Breaks (DSBs). Both proportion of γH2AX positive cells and frequency of γH2AX foci increased in ESCs or IPSCs as well as higher number of micronuclei as a mark of genomic instability.

Preferred agents are Bleomycin, ENU, alkylating agents, Actinomycin D, ROS-modulating agents, UV, H2O2, ionizing radiations (gamma rays, X rays), which all allow the induction and enhancement of mutation rates in pluripotent stem cells that accumulate during culture.

In a preferred embodiment, N-ethyl-N-nitrosourea (ENU) has been shown to create novel mutations and enhance the level of neo-antigens in treated pluripotent stem cells during long term culture at least from 7 to 60 days at a dose of <50 μg/ml. These mutations are similar to those reported in cancer.

It is thus possible to accumulate a diversity of mutations in response to DNA damage during pluripotent cells proliferation with a high rate of mutations from a selective advantage upon prolonged culture, while maintaining the pluripotency of the cells, in particular when the cells are cultured with HDACi in the medium. The presence of HDACis in culture preserves the increase active histones (H3K4me3 and H3K9ac) and epigenetic mark of pluripotency in response to inducing DNA damage, and the replication and proliferation rate during passages.

In another embodiment of the compositions and methods described herein, mutations are induced in the pluripotent cells through genetic modification of the cells with genes that promote high level of genomic instability. In particular, one can delete or reduce activity of genes or signaling pathways involved in DNA repair and replication, using appropriate inhibitors such as NER/BER/DSBR/MMR inhibitors. These methods that induce genomic instability linked to increased DNA damage may be performed by using "vectors" or by "genetic modification" that inactivate or knock down DNA repair related genes or signaling pathways such as DNA polymerase delta complex, mismatch repair (MMR), base excision repair (BER), Nucleotide excision repair (NER), homologous recombination (HR), DSBR or NEJH. Other examples of DNA repair genes are DNApkC, Ku70, Rad 51, Brca1 or Brca2.

In other embodiments, pluripotent cells are modified so as to repress apoptosis-associated genes such as p53 by genetic modification or chemical p53 such as Pifithrin-mu, Nutlin-3, or by using compounds that enhance cell survival such as Y-27632, a selective inhibitor of the p160-Rho-associated coiled kinase (ROCK).

In a particular embodiment, the population of pluripotent cells consists of induced pluripotent stem cells (iPSCs) that were generated from somatic cells, such as cells isolated from a patient, that already contained genomic alterations linked i) to DNA repair diseases including for example Ataxia telangiectasia, Bloom syndrome, Cockayne's syndrome, Fanconi's anaemia, Werner syndrome, Xeroderma pigmentosum, Nijmegen breakage syndrome;

ii) to hereditary family cancer syndromes with genomic instability, such Lynch syndrome (hereditary non-polyposis colorectal cancer with mutations in MMR genes including MLH1, MSH2, MSH6, PMS1, and PMS2), Li-Fraumeni with mutation in the TP53 gene or CHEK2, Hereditary Breast and Ovarian Cancer (HBOC) syndrome with deletion or mutation in BRCA1/2 gene, familial adenomatous polyposis (FAP) with mutations in APC gene;

iii) somatic oncogenic induced genomic instability as in CML with a translocation (T 9; 22).

In a preferred embodiment, the population of mutated pluripotent cells is made of induced pluripotent stem cells and generated from somatic cells containing genomic alterations linked to a disease. Typically, genomic alterations could be a translocation (T9:22), a deletion (BRCA1/2) or mutations (BRCA, RET).

In a particular embodiment, the population of pluripotent stem cells consists of iPSCs generated from cancer cell lines or patient-specific cancer cells.

In another embodiment, the population of ESCs or IPSCs is modified genetically to over-express multiple non-random cancer stem related neo-antigens by using «vectors». In particular embodiment, the population of ESCs or IPSCs is modified genetically to express multiple mutations and cancer stem cell specific neo-antigens (at least 5) in pluripotent stem cells by "genome editing" technology. The present invention provides compositions and methods providing ESCs or IPSCs by introducing of multiple neo-antigens thereof by RNA-guided multiplex genome editing, modification, inhibition of expression and other RNA-based technologies.

The term "genome editing" used here refers to the RNA mediated genetic manipulation including, in particular, a guide RNA for cas9-mediated genome editing. This guide RNA, (gRNA) is transfected along with an endonuclease cas9. The guide RNA provides the scaffold and a spacer sequence complementary to the target. In another embodiment genetic manipulation sequence can be a siRNA or a microRNA sequence designed for gene silencing according to standard methods in the art by the use of Crispr-Cas 9 systems. Compositions and methods for making and using Crispr-Cas systems are known in the art and described, in particular, in U.S. Pat. No. 8,697,359.

In a particular embodiment, the population of pluripotent cells is treated with alkylating agents. As used herein, the term "alkylating agents" refers to a substance which adds one or more alkyl groups from one molecule to another. This treatment creates new mutations in neo-antigens providing superior immune reactions by increasing oligo clonal expansion of TILs and Th1/Th2 cellular immunity.

In the present invention, an alkylating agent is selected from the group consisting of nitrogen mustards, nitrosoureas, alkyl sulfonates, triazines, ethylenimines, and combinations thereof Non-limiting examples of nitrogen mustards include mechlorethamine (Lundbeck), chlorambucil (GlaxoSmithKline), cyclophosphamide (Mead Johnson Co.), bendamustine (Astellas), ifosfamide (Baxter International), melphalan (Ligand), melphalan flufenamide (Oncopeptides), and pharmaceutically acceptable salts thereof. Non-limiting examples of nitrosoureas include streptozocin (Teva), carmustine (Eisai), lomustine (Sanofi), and pharmaceutically acceptable salts thereof. Non-limiting examples of alkyl sulfonates include busulfan (Jazz Pharmaceuticals) and pharmaceutically acceptable salts thereof. Non-limiting examples of triazines include dacarbazine (Bayer), temozolomide (Cancer Research Technology), and pharmaceutically acceptable salts thereof. Non-limiting examples of ethylenimines include thiotepa (Bedford Laboratories), altretamine (MGI Pharma), and pharmaceutically acceptable salts thereof. Other alkylating agents include ProLindac (Access), Ac-225 BC-8 (Actinium Pharmaceuticals), ALF-2111 (Alfact Innovation), trofosfamide (Baxter International), MDX-1203 (Bristol-Myers Squibb), thioureidobutyronitrile (CellCeutix), mitobronitol (Chinoin), mitolactol (Chinoin), nimustine (Daiichi Sankyo), glufosfamide (Eleison Pharmaceuticals), HuMax-TAC and PBD ADC combinations (Genmab), BP-C1 (Meabco), treosulfan (Medac), nifurtimox (Metronomx), improsulfan tosilate (Mitsubishi tanabe Pharma), ranimustine (Mitsubishi tanabe Pharma), ND-01 (NanoCarrier), HH-1 (Nordic Nanovector), 22P1G cells and ifosfamide combinations (Nuvilex), estramustine phosphate (Pfizer), prednimustine (Pfizer), lurbinectedin (PharmaMar), trabectedin (PharmaMar), altreatamine (Sanofi), SGN-CD33A (Seattle Genetics), fotemustine (Servier), nedaplatin (Shionogi), heptaplatin (Sk Holdings), apaziquone (Spectrum Pharmaceuticals), SG-2000 (Spirogen), TLK-58747 (Telik), laromustine (Vion Pharmaceuticals), procarbazine (Alkem Laboratories Ltd.), and pharmaceutically acceptable salts thereof. In another embodiment, the alkylating agent is selected from the group consisting of mechlorethamine (Lundbeck), chlorambucil (GlaxoSmithKline), cyclophosphamide (Mead Johnson Co.), streptozocin (Teva), dacarbazine (Bayer), thiotepa (Bedford Laboratories), altretamine (MGI Pharma), pharmaceutically acceptable salts thereof, and combinations thereof. In another embodiment, the alkylating agent is selected from the group consisting of ProLindac (Access), Ac-225 BC-8 (Actinium Pharmaceuticals), ALF-2111 (Alfact Innovation), bendamustine (Astellas), ifosfamide (Baxter International), trofosfamide (Baxter International), MDX-1203 (Bristol-Myers Squibb), temozolomide (Cancer Research Technology), thioureidobutyronitrile (CellCeutix), mitobronitol (Chinoin), mitolactol (Chinoin), nimustine (Daiichi Sankyo), carmustine (Eisai), glufosfamide (Eleison Pharmaceuticals), HuMax-TAC and PBD ADC combinations (Genmab), busulfan (Jazz Pharmaceuticals), melphalan (Ligand), BP-C1 (Meabco), treosulfan (Medac), nifurtimox (Metronomx), improsulfan tosilate (Mitsubishi tanabe Pharma), ranimustine (Mitsubishi tanabe Pharma), ND-01 (NanoCarrier), HH-1 (Nordic Nanovector), 22P1 G cells and ifosfamide combinations (Nuvilex), melphalan flufenamide (Oncopeptides), estramustine phosphate (Pfizer), prednimustine (Pfizer), lurbinectedin (PharmaMar), trabectedin (PharmaMar), altreatamine (Sanofi), lomustine (Sanofi), SGN-CD33A (Seattle Genetics), fotemustine (Servier), nedaplatin (Shionogi), heptaplatin (Sk Holdings), apaziquone (Spectrum Pharmaceuticals), SG-2000 (Spirogen), TLK-58747 (Telik), laromustine (Vion Pharmaceuticals), procarbazine (Alkem Laboratories Ltd.), pharmaceutically acceptable salts thereof, and combinations thereof.

In a particular embodiment, the population of pluripotent cells is treated with N-ethyl-N-nitrosourea (ENU, CAS Number 759-73-9). ENU has the following chemical formula $C_3H_7N_3O_2$, is a highly potent mutagen by transferring the ethyl group to nucleobases in nucleic acids.

As indicated above, the purpose of the mutagenic agent is to introduce random mutations in genes of the pluripotent cells during expansion (introduction of mutations occurs during the replication and division of the cells). The population of pluripotent stem cell acquires mutations that may provide a growth advantage and are selected for to promote culture adaptation. Passages of ESCs or iPSCs undergo a high level of selection pressure, and upon expansion multiple clonal mutated population may be favorably selected for.

It is to be noted that, since the pluripotent cells are very stable, application of the mutagen may have to be performed for a long period of time. As a matter of illustration, when ENU is used, it may be applied for at least 7 days, more preferably at least 15 days, more preferably at least 20 days, more preferably at least 30 days, more preferably at least 40 days, more preferably at least 50 days or even at least 60 days. After application of the mutagen, the cells are washed (if the mutagen is a chemical agent) and can be further expanded, in the presence of the agent that favors MHC-I expression, in particular a HDACi. This agent is preferably also present during application of the mutagenic agent.

It can thus be observed and checked that the mutagen will induce mutations (i.e non-synonymous, nonsense, frameshift, StopGain, splice variant, CNVs, SNVs) in some of the embryogenic genes that are expressed by the pluripotent cells and hence increase the diversity of these antigens (new neo-antigens within the whole genome). This will thus increase the possibility of the vaccine composition with enhanced immunogenicity, able to stimulate a broad immune response against aggressive cancers where there are rapid and frequent mutations.

An efficient immune response may indeed be difficult to obtain for some cancer where clonal expansion of cancer cells occurs with mutations in the antigens expressed by the tumor cells.

The immune response would thus depend in the mutational load of the cancer. The generation of random mutations in the pluripotent cell population by the use of the mutagen would thus lead to expression of mutated embryonic antigens and increase the diversity of the antigens presented to the immune system upon vaccination.

Consequently, there would already be primed T-cells against mutated antigens that would appear in the cancer cells during division of such cells, which would speed-up and improve the immune response against these cells.

Modification of Pluripotent Cells

In a particular embodiment, the population of pluripotent stem cells is modified genetically to over-express compounds which stimulate immune response by using gene integration within the pluripotent cell genome. Typically, in the first step, the population of stem cells is isolated and expanded. In the second step, the genes of interest are packaged into integrative viral vectors, such as retroviruses or lentiviruses. In the third step, integrative viral vectors containing the interest gene are transferred to the population of stem cells.

In a particular embodiment, the population of pluripotent cells is modified with the genes of proteins which stimulate MHC expressions and/or immune response. These compounds are selected from the group consisting of interferon alpha (IFN-α), an interferon gamma (IFN-γ), an interleukin 2 (IL-2), an interleukin 4 (IL-4), an interleukin 6 (IL-6), an interleukin 12 (IL-12), a tumor necrosis factors (TNFs), and a granulocyte-macrophage colony stimulating factor (GM-CSF), functional fragments thereof, and combinations thereof.

Interferons (IFNs) contemplated by the present invention include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behavior and/or increasing their production of antigens thus making the cancer cells easier for the immune system to recognize and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation).

Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention.

Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin).

In its broadest sense, a "vector" is any vehicle capable of facilitating the transfer of the oligonucleotides to the cells. Preferably, the vector transports the nucleic acid to cells with reduced degradation relative to the extent of degradation that would result in the absence of the vector. In general, the vectors useful in the invention include, but are not limited to, naked plasmids, non-viral delivery systems (electroporation, sonoporation, cationic transfection agents, liposomes, etc. . . . ), phagemids, viruses, other vehicles derived from viral or bacterial sources that have been manipulated by the insertion or incorporation of the nucleic acid sequences. Viral vectors are a preferred type of vector and include, but are not limited to nucleic acid sequences from the following viruses: RNA viruses such as a retrovirus (as for example moloney murine leukemia virus and lentiviral derived vectors), harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus. One can readily employ other vectors not named but known to the art.

Typically, in the context of the invention, viral vectors include adenoviruses and adeno-associated (AAV) viruses, which are DNA viruses that have already been approved for human use in gene therapy. Actually 12 different AAV serotypes (AAV1 to 12) are known, each with different tissue tropisms (Wu, Z Mol Ther 2006; 14:316-27). Recombinant AAV are derived from the dependent parvovirus AAV (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hematopoietic cells; and lack of superinfection inhibition thus allowing multiple series of transductions. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by, intranasal sprays or drops, rectal suppository and orally. Preferably, said DNA plasmid is injected through an intraocular way (intravitreal, sub retinal, suprachoroidal . . . ). It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a particular embodiment, the population of stem cells is modified by the introduction of the transgene such as siRNA into the AAVS1 locus of chromosome 19 by homologous recombination.

The term "homologous recombination" as used herein refers to a gene targeting means for artificially modifying a specific gene on a chromosome or a genome. When a genomic fragment having a portion homologous to that of a target sequence on the chromosome is introduced into cells, the term refers to recombination that takes place based on the nucleotide sequence homology between the introduced genomic fragment and the locus corresponding thereto on the chromosome.

Also, the term "genetic modification" refers to, in the locus of a desired gene on the chromosome, the insertion of an exogenous DNA, the substitution of a portion of or the whole of the gene with an exogenous DNA, or the deletion of the gene. More specifically, genetic modification refers to the insertion (that is, "knock-in") of an exogenous DNA fragment while the endogenous DNA sequence is retained in a manner such that the fragment is expressed in conjunction with the expression of a gene at a specific locus or is expressed constitutively, or, the substitution, deletion, or disruption (that is, "knock-out") of a portion of or the whole gene sequence so as to modify the endogenous DNA sequence.

Examples of methods for introducing an artificial chromosome into cells include a calcium phosphate precipitation method (Graham et al., (1978) Virology 52: 456-457, Wigler et al., (1979) Proc. Natl. Acad. Sci. U.S.A. 76 1373-1376 and Current Protocols in Molecular Biology Vol. 1, Wiley Inter-Science, Supplement 14, Unit 9.1.1-9.1.9 (1990)), a fusion method using polyethylene glycol (U.S. Pat. No. 4,684,611), a method using lipid carriers such as lipofection (Teifel et al., (1995) Biotechniques 19: 79-80, Albrecht et al., (1996) Ann. Hematol. 72: 73-79; Holmen et al., (1995) In Vitro Cell Dev. Biol. Anim. 31: 347-351, Remy et al., (1994) Bioconjug. Chem. 5: 647-654, Le Bolc'het al., (1995) Tetrahedron Lett. 36: 6681-6684, Loeffler et al., (1993) Meth. Enzymol, 217: 599-618 and Strauss (1996) Meth. Mol. Biol. 54: 307-327), electroporation, and methods for fusion with microcells (U.S. Pat. Nos. 5,240,840, 4,806, 476, 5,298,429, and 5,396,767, Fournier (1981) Proc. Natl. Acad. Sci. U.S.A. 78: 6349-6353 and Lambert et al., (1991) Proc. Natl. Acad. Sci. U.S.A. 88: 5907-59).

Population of Cells

Thus, with the methods as described above, the inventors have obtained a population of pluripotent cells expressing new embryonic epitopes within partial or all the embryonic genes that will trigger a more efficient antitumor immunity. More particularly, the inventors have shown that the population of pluripotent cells treated with N-ethyl-N-nitrosourea (ENU) presents random mutations compared to the population of pluripotent cells without treated with ENU. Accordingly, this population is also a subject of the invention.

The invention thus relates to a composition of cells comprising pluripotent cells, wherein cells in said population presents a mutation rate of at least 0.1%, preferably at least 1%, more preferably at least 2%, more preferably at least 5%, more preferably at least 10%, more preferably at least 15%, more preferably at least 20%, more preferably at least 30%, more preferably at least 40%, or even at least 50%, in at least three genes, more preferably at least four genes, more preferably at least five genes, more preferably at least six genes, more preferably at least seven genes, selected from the following group consisting of TP53, P2RY8, CRLF2, CRTC3, BLM, ASXL1, IDH2, NTRK3, MALAT1, EXT1, NCOA2, IKF1, PIK3R1, EP300, AKT2, PPP2R1A, CDK12, BRCA1, ERB2, CDH1, TBX3, SMARCD1, HSP90AA1, EZH2, SUZ12, STAT5B and POUF5F1.

This mutation rate of the genes is studied in the cell population, after exposure to the mutagenic agent, before or after further expansion, if such further expansion is performed.

Due to the fact that the pluripotent cells are genetically very stable, the presence of a high amount of mutations in at least three genes as listed above demonstrates the presence of a new population of pluripotent cells that didn't preexist and would not be observed in the absence of the mutagenic conditions.

Exposure of the cells to the mutagenic agent will trigger apparition of random mutations in the genome of such cells. The population resulting from such exposure will thus be heterogeneous, as compared to a population of pluripotent cells that is essentially homogenous, due to the low rate of natural mutations during long term expansion and culture. The population herein obtained is thus characterized in particular in that:
  The cells are pluripotent (i.e. bear the markers of pluripotency)
  There are multiple differences in the genome of the cells in the population, as indicated above, i.e. it is possible to detect a rate (as indicated above) of mutated genes as listed above, within the cells of the population.
As a matter of illustration, a mutation rate of 5% of the TP53 gene means that 95% of the TP53 sequences in the cell population are identical (called TP53 reference sequence), and the last 5% of the TP53 sequence are different from the TP53 reference sequence.

In a further embodiment, the invention thus relates to a composition of cells comprising pluripotent cells, wherein cells in said population present a mutational landscape in the population of ESCs or IPSCs comprising one or more of the following features:
  i) At least >3 (or more as seen above) cancer related neo-antigens mutations introduced genetically in ESCs or IPSCs by genomic modification.
  ii) A combination of mutation types restricted to cancer genome induced by mutagen agents and enriched by a selective advantage in cultured embryonic pluripotent stem cells.
Mutagen process is causing increased levels of novel genomic mutations and genetic mosaicism in the resultant late-passage human iPS cell lines.
Analysis of the mutations in the genes is preferably performed by large scale genomic analysis of induced cancer related "mutanome" signature, in each ESCs and IPSCs population, by NGS (Exome, RNAseq or Whole-genome sequencing), CGH array, SNP arrays. Whole-exome sequencing in combination with transcriptome profiling enables the description of the expressed protein coding mutanome.
Genomic aberrations are identified by using at least 2 algorithms for bioinformatic analysis, known in the art. The prevalence of total mutations in the whole genome after application of the mutagen agents will confirm the higher mutation and/or CNV load in output ESCs or IPSCs.
Qualitative and quantitative criteria will allow defining each cell population within genetic mosaicism in ESCs or IPSCs as described:
Qualitative criteria include:
  Identification of acquired novel molecular somatic alterations (mutations, CNVs or SNVs) defined regarding their presence in ESCs or IPSs genome after mutagenesis and their absence in ESCs or IPSCs without mutagenesis in similar cultured passages.
  Classification of each novel mutations (i.e non-synonymous, nonsense, splice variant,
  CNVs, SNVs) and validation by their overlapping detection in cancer genome (from data base i.e. TCGA, ICGC, COSMIC) and present in pluripotent genes and embryonic pathways (according pluripotency genes i.e Plurinet gene).
Quantitative criteria such include:
  The prevalence of these novel somatic mutations (with false discovery rate confidence value FDR≤0.05) and novel CNVs/SNVs (with FDR<10%) in the whole genome is defined for each ESCs or IPSs.
  The presence of validated mutation in at least >3 different genes
  The mutation rate of each novel and stable somatic mutations with an allelic frequency from at least from >0.1%, or other percentages as seen above, up to 50% after clonal selection and expansion or regarding the number of passages (from 50x depth to 100xdepth and 80-98% of target exome coverage).
  The expression of Pluripotency markers and a gene-expression based assay (PluriTest) with at least >90% of expression rate compared to input ESCs or IPSCs before mutagenesis or genetic modification.
  Expression of MHC I molecules at the cell surfaces (for instance as determined by FACS) being increased of at least 50%, and generally up to 90% as compared to a cell population expanded in the absence of HDACi, in particular VPA.

The present invention relates to vaccine composition that includes a population of pluripotent cells, as disclosed above and an agent that stimulates immune response and/or MHC I expression.

In particular, such pluripotent cells are ESCs or IPSCs, preferably inactivated, and optionally mutated, as disclosed above.

The agent that stimulates immune response may be an adjuvant (immunostimulant) as known in the art. It is preferably a HDACi (used at a dose range comprised between 0.2 mM and 4 mM). When such HDACi is used, another adjuvant may also be used.

The invention also relates to a device (such as a syringe) containing such vaccine composition, that can be used for a simultaneous administration of the HDACi compound and the cell composition.

Such vaccine composition can be used as a therapeutic vaccine against a stem cell cancer (cancer, the cells of which express neoantigens), for cure of the patient, or as a prophylactic vaccine, to prevent onset of such cancers, in particular in patients susceptible to these cancers.

Predisposition genes are, for instance (see also Lindor et al, 2008 Journal of the National Cancer Institute Monographs, No. 38, Concise Handbook of Familial Cancer Susceptibility Syndromes, Second Edition):
Breast/ovary: BRCA1, BRCA2, PALB2, RAD51
Lynch syndrome: MLH1, MSH2, MSH6, PMS2, EPCAM
Hereditary Papillary Renal Cell Carcinoma: FH, MET
Cowden disease: PTEN, PIK3CA
Fanconi disease: FANC
Von Hippel-Lindau disease: VHL
Malicious melanoma: CDKN2A, MITF, BAP1, CDK4
Endocrine Neoplasia: MEN1, RET, CDKN1B
Neurofibromatosis: NF1, NF2, LZTR1, SMARCB1, SPRED1
hereditary pheochromocytome paragangliome: SDH, TMEM127, MAX, EPAS1
Familial adenomatous polyposis: APC, MUTYH
Retinoblastoma: RB1
Birt-hogg-dube syndrome: FLCN
Bloom syndrome: BLM
Carney syndrome: PRKAR1A
Gorlin syndrome: PTCH1
Li-Fraumeni syndrome: TP53, CHEK2
Nijmegen syndrome: NBN
Peutz-Jeghers Syndrome: STK11
Familial Juvenile Polyposis: BMPR1A, SMAD4
Xeroderma pigmentosum: XP
This list is not limitative.

In certain embodiment, cancer stem vaccine product comprise a mixture of cell lysate after lyophylisation, a mixture of enriched multi-cancer stem neoantigens, purified cancer stem neo-antigens, exosomes derived from ESCs or IPSCs, DNA, RNA Proteins or multiple peptides from engineered ESCs or IPSCs. These are the immunogenic agent as disclosed above, which are formulated in the presence of HDACi.

In another embodiment, cancer stem cell vaccine product is mixed with supernatant GMP media from engineered irradiated ESCs or IPSCs used as an adjuvant effector.

In a preferred embodiment, the cells in this composition are inactivated (i.e. can not divide anymore).

The composition of cells of the invention is susceptible to be obtained by any of the methods as disclosed above.

It is to be noted that the cells in this composition are heterogeneous in nature, when the mutagen has been used and hence differ from a pluripotent cell composition that has been cultured according to methods known in the art, and which is homogenous.

When it has been cultured in the absence of a mutagen, the population of cell differs from a population of cells that has been cultured according to methods known in the art, as the presence of the agent maintaining expression of pluripotent genes and increasing MHC I presentation, in the culture medium, will lead to cells that have more of these MHC I molecules on their surface.

As used herein the term "compound selected from a group which activates MHC expression and/or immune response" refers to compounds which are capable of stimulating immunogenicity. Such compound is called activator of MHC expression and/or immune response. The term "MHC" refers to major histocompatibility complex which is present on the cell surface to recognize foreign molecules, called antigens. MHC binds to antigens and present them to immune molecules such as lymphocytes T and B. The term "immune response" refers to immunological response of immune system to an antigen. By activating the immune response, the population of FoxP3 subpopulation and myeloid-derived suppressor cell (MDSC) are decreased and, in contrary the NK population is increased. In the context of the invention, the immune response against tumors comprises a cytotoxic T cell response against an antigen present in or on a cell of the tumor. In some embodiments, the cytotoxic T cell response is mediated by CD8+ T cells. Typically, in the context of the invention, the antigen which activates the MHC expression and/or immune response corresponds to the molecules present on the population of pluripotent cells as described above. The compound which activates the MCH expression and/or immune system is a neo-antigen. The term "neo-antigen" or "neo-antigenic" means a class of antigens that arises from at least one mutation which alters the amino acid sequence of genome encoded proteins In the context of the invention, compounds are selected from the group consisting of: cytokines, histone deacetylase inhibitors, DNA methyltransferase inhibitors, and histone-lysine N-methyltransferase enzyme inhibitors.

In a particular embodiment, the activator of MHC expression and/or of immune response is a histone deacetylase inhibitor.

As used herein, the term histone "histone deacetylase inhibitor" called also HDACi, refers to a class of compounds that interfere with the function of histone deacetylase. Histone deacetylases (HDACs) play important roles in transcriptional regulation and pathogenesis of cancer. Typically, inhibitors of HDACs modulate transcription and induce cell growth arrest, differentiation and apoptosis. HDACis also enhance the cytotoxic effects of therapeutic agents used in cancer treatment, including radiation and chemotherapeutic drugs.

In a particular embodiment, the histone deacetylase inhibitor is valproic acid (VPA).

The term "valproic acid" refers to acid-2-propylpentanoic ($C_8H_{16}O_2$), which has the following CAS number and formula 99-66-1 in the art::

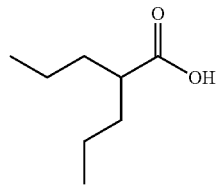

The biological activities of valproic acid are multiple (Chateauvieux et al, J. Biomed. Biotechnol, 2010, pii: 479364. doi: 10.1155/2010/479364). Valproic acid affects the neurotransmitter GABA (Gamma Amino Butyrate) potentiating inhibitory activity. Several mechanisms of action are suggested. Valproic acid is particularly the GABA metabolism: inhibits degradation of GABA, GABA Transaminobutyratre (LAMP), acroissement of GABA synthesis, and modifies its turnover. In addition, valproic acid blocks certain ion channels, reduces arousal mediated by the N-Methyl-D-Aspartate, and blocks the activity of ion channels including Na+ and Ca 2+(voltage-dependent L-type CACNA1 type C, D, N, and F).

In the context of the invention, valproic acid is used as an immune-stimulant to boost immune response against cancers expressing pluripotent antigens shared with human embryonic stem cells (ESCs) or induced pluripotent stem cells (IPSCs).

More particularly, VPA is used to stimulate and enhance the expression of MHC-I on cancer stem cell compartment, increasing the neo-antigen content in the CSC compartment. Higher expression of MHC I in ESCs and IPSCs and in CSCs allow to enhance the presentation of neo-antigens associated with MHC-I to APC/Dendritic cells to induce TH1 immune response. Higher level of chemokines (CXCL9, CXCL10 . . . ) allow to enhance the recruitment of T cell into the tumor.

The present invention relates to methods to increase the neo-antigen content in the CSC compartment expression of embryonic antigens in CSC and tumor cells through chromatin remodelling, as well as chemokines expression (CXCL9, CXCL10 . . . ) by expanding pluripotent cells in the presence of an HADCi such as VPA and/or 5 Azacytidine.

In particular, when used for treating a patient in vivo, the present compositions and vaccines makes it possible to modify the tumor microenvironment and promote the recruitment of T cells into the tumor, so as to obtain a long term durable reduction of tumor volume.

This is due to a synergistic effect of the cancer primed pluripotent cell vaccine and VPA co-administration, that is further improved when the HDACi is further administered to the patient, for a period of time (such as at least 15 days) after vaccine injection. The examples show that combined treatment by both cancer stem cell vaccine and VPA provide a superior anti-tumor response by increasing TILs with Th1/Th2 cellular immunity, decreasing FoxP3 TReg subpopulation, activating NK cells and decreasing the suppressive action of MDSC, while reversing the tumor immune suppression and decrease the TReg (in tumor and spleen) and recruiting T CD4+ and CD8+ lymphocytes into the tumor with a less proportion of T CD4 and CD8 expressing PD-1.

VPA may down regulate c-Myc expression level and potentially induce apoptosis and autophagy of cancer cells and CSCs. VPA may boost the adaptive immune response via autophagosome cross-presentation.

A well other known action of VPA is the decrease of inflammation cytokines such as IL6, IL8, TNFa interleukin (IL)-1beta, IL-17 in the lymph nodes.

In a particular embodiment, the histone deacetylase inhibitor is suberoylanilide hydroxamic acid, also called Vorinostat (N-Hydroxy-N'-phenyloctanediamide) was the first histone deacetylase inhibitor approved by the U.S. Food and Drug Administration (FDA) on 2006 (Marchion D C et al 2004; Valente et al 2014).

In a particular embodiment the histone deacetylase inhibitor is Panobinostat (LBH-589) has received the FDA approval on 2015 and has the structure as described in Valente et al 2014.

In a particular embodiment the histone deacetylase inhibitor is Givinostat (ITF2357) has been granted as an orphan drug in the European Union (Leoni et al 2005; Valente et al 2014).

In a particular embodiment the histone deacetylase inhibitor is Belinostat also called Beleodaq (PXD-101) has received the FDA approval on 2014 (Ja et al 2003; Valente et al 2014).

In a particular embodiment the histone deacetylase inhibitor is Entinostat (as SNDX-275 or MS-275). This molecule has the following chemical formula ($C_{21}H_{20}N_4O_3$) and has structure as described in Valente et al 2014.

In a particular embodiment the histone deacetylase inhibitor is Mocetinostat (MGCD01030) having the following chemical formula ($C_{23}H_{20}N_6O$) (Valente et al 2014).

In a particular embodiment the histone deacetylase inhibitor is Practinostat (SB939) having the following chemical formula ($C_{20}H_{30}N_4O_2$) and the structure as described in Diermayr et al 2012.

In a particular embodiment the histone deacetylase inhibitor is Chidamide (CS055/HBI-8000) having the following chemical formula ($C_{22}H_{19}FN_4O_2$).

In a particular embodiment the histone deacetylase inhibitor is Quisinostat (JNJ-26481585) having the following chemical formula ($C_{21}H_{26}N_6O_2$).

In a particular embodiment the histone deacetylase inhibitor is Abexinostat (PCI24781) having the following chemical formula ($C_{21}H_{23}N_3O_5$) (Valente et al 2014).

In a particular embodiment the histone deacetylase inhibitor is CHR-3996 having the following chemical formula ($C_{20}H_{19}FN_6O_2$) (Moffat D et al 2010; Banerji et al 2012). In a particular embodiment the histone deacetylase inhibitor is AR-42 having the following chemical formula ($C_{18}H_{20}N_2O_3$) (Lin et al 2012).

In a particular embodiment, the activator of MHC expression is DNA methyltransferase inhibitors.

As used herein, the term "DNA methyltransferase inhibitors" refer to compounds which are capable of interacting with DNA methyltransferase (DNMT) and inhibiting their activity. DNMT are the enzymes which catalyze the transfer of a methyl group to DNA. DNA methylation serves a wide variety of biological functions. All the known DNA methyltransferases use S-adenosyl methionine (SAM) as the methyl donor.

In a particular embodiment, the DNA methyltransferase inhibitor is azacytidine, also known as 5-aza-2-deoxycytidine having the following chemical formula ($C_8H_{12}N_4O_5$) and structure in the art (Kaminskas et al 2004; Estey et al 2013).

In a particular embodiment, the DNA methyltransferase inhibitor is decitabine also known as 5-aza-2'-deoxycytidine, having the following formula ($C_8H_{12}N_4O_4$) (Kantarjian et al 2006).

In a particular embodiment, the activator of MHC expression and/or immune response is a histone-lysine N-methyltransferase enzyme inhibitor, or DNA methyltransferase inhibitor. As used herein, the term "histone-lysine N-methyltransferase enzyme inhibitor" refers to compounds which are capable of interacting with histone-lysine N-methyltransferase enzyme encoded by Enhancer of zeste homolog 1 (EZH1) and 2 (EZH2) gene that participates in DNA methylation. EZH2 catalyzes the addition of methyl groups to histone H3 at lysine 27 by using the cofactor S-adenosyl-L-methionine.

In a particular embodiment, the histone-lysine N-methyltransferase enzyme inhibitor is 3-Deazaneplanocin A (DZNep, C-c3Ado). DZNep, C-c3Ado has the following chemical formula $C_{12}H_{14}N_4O_3$ and CAS number 102052-95-9 in the art.

In a particular embodiment, the histone-lysine N-methyltransferase enzyme inhibitor is UNC1999 and an inactive analog compound. UNC1999 has the following chemical formula $C_{33}H_{43}N_7O_2$ and CAS number 1431612-23-5 in the art.

In a particular embodiment, the histone-lysine N-methyltransferase enzyme inhibitor is UNC2400 and an inactive analog compound. UNC2400 has the following chemical formula $C_{35}H_{47}N_7O_2$ and CAS number 1433200-49-7 in the art.

In a particular embodiment, the histone-lysine N-methyltransferase enzyme inhibitor is tazemetostat (EPZ6438, E7438). Tazemetostat has the following chemical formula $C_{34}H_{44}N_4O_4$ and CAS number 1403254-99-8 in the art.

In a particular embodiment, the histone-lysine N-methyltransferase enzyme inhibitor is trifluoroacetate (EPZ011989). Trifluoroacetate has the following chemical formula $CF_3COONa$ and CAS number 2923-18-4 in the art.

In a particular embodiment, the histone-lysine N-methyltransferase enzyme inhibitor is EPZ005687. EPZ005687 has the following chemical formula $C_{32}H_{37}N_5O_3$ and CAS number 1396772-26-1 in the art.

In a particular embodiment, histone-lysine N-methyltransferase enzyme inhibitor is GSK343. GSK343 has the following chemical formula $C_{31}H_{39}N_7O_2$ and CAS number 1346704-33-3 in the art.

In a particular embodiment, histone-lysine N-methyltransferase enzyme inhibitor is GSK126. GSK126 has the following chemical formula $C_{31}H_{38}N_6O_2$ and CAS number 1346574-57-9 in the art.

In a particular embodiment, histone-lysine N-methyltransferase enzyme inhibitor is GSK2816126. GSK2816126 has the following chemical formula $C_{31}H_{38}N_6O_2$ and CAS number 1346574-57-9 in the art.

In a particular embodiment, histone-lysine N-methyltransferase enzyme inhibitor is ZLD1039. ZLD1039 has the following chemical formula $C_{36}H_{48}N_6O_3$ and CAS number 1826865-46-6 in the art.

It is also envisaged to use both a HDACi and a DNA methyltransferase inhibitor.

Indeed, it has been shown that the combined use of VPA and 5-Azacytidine (an analog of the nucleoside cytidine which can be incorporated into DNA and RNA) leads to a synergetic effect on the re-expression of neo anti-embryonic antigens.

The HDACi is administered in a therapeutically efficient amount. For VPA, it may be from 10 to 15 mg/kg/day, up to 60 mg/kg/day. The plasma level of VPA should preferably be in the usually accepted therapeutic range (50 to 100 μg/mL).

In a further aspect, the method according to the invention is suitable to treat cancers expressing a large number of embryonic antigens which share the expression with human embryonic stem cells (hESC) or human induced Pluripotent Stem Cells (hiPSCs). (e.g. Embryonic Antigen-3 (SSEA3), SSEA4, TRA-1-60, TRA-1-81, Oct4, Sox2, Klf4, Nanog, Lin28 . . . ).

As used herein, the terms "cancers expressing human stems cells", are the cancers that are preferably targeted by the methods, vaccines and compositions herein disclosed, refer to cancer stem cells expressing a large number of embryonic antigens which share the expression with human embryonic stem cells (hESCs) or induced pluripotent stem cells (iPSCs). Typically, the cancer is selected from the group consisting of bladder carcinoma, breast carcinoma, cervical carcinoma, cholangiocarcinoma, colorectal carcinoma, gastric sarcoma, glioma, lung carcinoma, lymphoma, acute and chronic lymphoid and myeloid leukemias, melanoma, multiple myeloma, osteosarcoma, ovarian carcinoma, pancreatic carcinoma, prostate carcinoma, stomach carcinoma, kidney carcinoma, a head and neck tumor, and a solid tumor.

As used herein the terms "administering" or "administration" refer to the act of injecting or otherwise physically delivering a substance as it exists outside the body (e.g., combined preparation) into the subject, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

In the preferred embodiment, the vaccine composition (pluripotent cells+agent stimulating MHC presentation) is injected subcutaneously. Injection may be simultaneous, sequential, separate, at the same injection point or at different injection points, in the same syringe, or in separate syringes . . . .

In a preferred embodiment, the follow-up treatment (administration of the compound that stimulates MHC I and/or immune system, such as an HDACi, in particular VPA) is administered by the oral route.

A "therapeutically effective amount" is intended for a minimal amount of active agent which is necessary to impart therapeutic benefit to a subject. For example, a "therapeutically effective amount" to a subject is such an amount which induces, ameliorates or otherwise causes an improvement in the pathological symptoms, disease progression or physiological conditions associated with or resistance to succumbing to a disorder. It will be understood that the total daily usage of the compounds of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In a particular embodiment, the method according to the invention comprises further one or more of radiation therapy, targeted therapy, immunotherapy, or chemotherapy. Typically, the physician could choose to administer the subject with i) a population of pluripotent cells and ii) a compound selected from a group which activates MHC expression and/or immune response, as a combined preparation with radiation therapy, targeted therapy, immunotherapy, or chemotherapy.

In some embodiments, the subject is administered with i) a population of pluripotent cells and ii) a compound selected from a group which activates MHC expression and/or immune response, as a combined preparation and a chemotherapeutic agent.

The term "chemotherapeutic agent" refers to chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a carnptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridin A and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.].) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit honnone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the subject is administered with i) a population of pluripotent cells and ii) a compound selected from a group which activates MHC expression and/or immune response, as a combined preparation and a targeted cancer therapy.

Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names. In some embodiments, the targeted therapy consists of administering the subject with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signalling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), bevacizumab (avastin), MK-2206 (8-[4-aminocyclobutyl)phenyl]-9-phenyl-1,2,4-triazolo[3,4-f][1,6]naphthyridin-3(2H)-one hydrochloride) derivatives thereof, analogs thereof, and combinations thereof. Additional tyrosine kinase inhibitors and related compounds suitable for use in the present invention are described in, for example, U.S Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In certain embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the subject is administered with i) a population of pluripotent cells and ii) a compound selected from a group which activates MHC expression and/or immune response, as a combined preparation and an immune checkpoint inhibitor.

As used herein, the term "immune checkpoint inhibitor" refers to molecules that totally or partially reduce, inhibit, interfere with or modulate one or more checkpoint proteins. Checkpoint proteins regulate T-cell activation or function. Numerous checkpoint proteins are known, such as CTLA-4 and its ligands CD80 and CD86; and PD1 with its ligands PDL1 and PDL2 (Pardoll, Nature Reviews Cancer 12: 252-264, 2012). These proteins are responsible for costimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies. In some embodiments, the immune checkpoint inhibitor is an antibody selected from the group consisting of anti-CTLA4 antibodies (e.g. Ipilimumab), anti-PD1 antibodies (e.g. Nivolumab, Pembrolizumab), anti-PDL1 antibodies, anti-TIM3 antibodies, anti-LAG3 antibodies, anti-B7H3 antibodies, anti-B7H4 antibodies, anti-BTLA antibodies, and anti-B7H6 antibodies. Examples of anti-CTLA-4 antibodies are described in U.S. Pat. Nos. 5,811,097; 5,811,097; 5,855,887; 6,051,227; 6,207,157; 6,682,736; 6,984,720; and 7,605,238. One anti-CTLA-4 antibody is tremelimumab, (ticilimumab, CP-675, 206). In some embodiments, the anti-CTLA-4 antibody is ipilimumab (also known as 10D1, MDX-D010) a fully human monoclonal IgG antibody that binds to CTLA-4. Another immune checkpoint protein is programmed cell death 1 (PD-1). Examples of PD-1 and PD-L1 blockers are described in U.S. Pat. Nos. 7,488,802; 7,943,743; 8,008, 449; 8,168,757; 8,217,149, and PCT Published Patent Application Nos: WO03042402, WO2008156712, WO2010089411, WO2010036959, WO2011066342, WO2011159877, WO2011082400, and WO2011161699. In some embodiments, the PD-1 blockers include anti-PD-L1 antibodies. In certain other embodiments, the PD-1 blockers include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224 is a fusion protein of B7-DC; an antibody Fc portion; BMS-936559 (MDX-1105-01) for PD-L1 (B7-H1) blockade. Other immune-checkpoint inhibitors include lymphocyte activation gene-3 (LAG-3) inhibitors, such as IMP321, a soluble Ig fusion protein (Brignone et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo et al., 2012, Clin. Cancer Res. July 15 (18) 3834). Also included are TIM3 (T-cell immunoglobulin domain and mucin domain 3) inhibitors (Fourcade et al., 2010, J. Exp. Med. 207:2175-86 and Sakuishi et al., 2010, J. Exp. Med. 207:2187-94). In some embodiments, the immunotherapeutic treatment consists of an adoptive immunotherapy, as described by Nicholas P. Restifo, Mark E. Dudley and Steven A. Rosenberg ("Adoptive immunotherapy for cancer: harnessing the T cell response, Nature Reviews Immunology, Volume 12, April 2012). In adoptive immunotherapy, the patient's circulating lymphocytes, or tumor-infiltrated lymphocytes, are isolated in vitro, activated by lymphokines such as IL-2 and readministered (Rosenberg et al., 1988; 1989). The activated lymphocytes are most preferably be the patient's own cells that were earlier isolated from a blood sample and activated (or "expanded") in vitro.

In some embodiments, the subject is administered with i) a population of pluripotent cells and ii) a compound selected from a group which activates MHC expression and/or immune response, as a combined preparation and a radiotherapeutic agent.

The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

Pharmaceutical and Vaccine Compositions

The compounds which activate MHC expression and/or immune response and the population of pluripotent cells as described above may be combined with pharmaceutically acceptable excipients, and optionally sustained-release matrices, such as biodegradable polymers, to form pharmaceutical compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The polypeptide (or nucleic acid encoding thereof) can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

More particularly, the population of pluripotent cells and the compound which activates MHC expression and/or immune response are formulated on a vaccine composition. Accordingly, the invention relates to a vaccine composition comprising i) a population of pluripotent cells and ii) a compound selected from a group which activates MHC expression and/or immune response.

In a particular embodiment, the vaccine composition according to the invention comprising i) human embryonic stem cells and ii) acid valproic.

In a particular embodiment, the vaccine composition according to the invention comprising i) induced pluripotent stem cells (iPSCs) expressing neo-antigens, in particular enhanced by mutagen agents or genetic modification and ii) valproic acid.

The composition may also comprise 5 Azacytidine.

Moreover, the vaccine composition of the present invention can be used in a subject suffering from a cancer as described above.

The vaccine composition according to the invention can be formulated with the physiological excipients set forth above in the same manner as in the immunogenic compositions. For instance, the pharmaceutically acceptable vehicles include, but are not limited to, phosphate buffered saline solutions, distilled water, emulsions such as an oil/water emulsions, various types of wetting agents sterile solutions and the like. Adjuvants such as muramyl peptides such as MDP, IL-12, aluminium phosphate, aluminium hydroxide, Alum and/or Montanide® can be used in the vaccines.

The vaccine composition according to the invention can be administered subcutaneous (s.c), intradermal (i.d.), intramuscular (i.m.) or intravenous (i.v.) injection, oral administration and intranasal administration or inhalation. The administration of the vaccine is usually in a single dose.

Alternatively, the administration of the vaccine of the invention is made a first time (initial vaccination), followed by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 recalls (subsequent administration), with the same population of stem cells, the compound which stimulates the immune system or a combination of thereof and/or with a further one or more of radiation therapy, targeted therapy, immunotherapy, or chemotherapy.

The vaccine composition is also provided in a kit. The kit comprises the vaccine composition and an information leaflet providing instructions for immunization. The kit comprises also the all materials for the administration of the products.

The invention will be further illustrated by the following figures and examples. However, these examples and figures should not be interpreted in any way as limiting the scope of the present invention.

EXAMPLES

Example 1

It was reported that fetal tissues can be used to immunize mice that are able to reject transplantable tumors including cancer of the skin, liver, and gastrointestinal tract. This response is explained by the fact that those tumor cells express a high number of oncofetal antigens. To date several human cancer vaccine trials have been set up in order to target embryonic antigens such as carcinoembryonic antigen (CEA) and alpha fetoprotein or cancer/testes antigens. Unfortunately, targeting one antigen alone was shown to be not efficient enough to generate strong antitumor immune responses to mediate tumor rejection because of rapid appearance of escape mutants and the general inefficiency of monovalent cancer vaccines. Recent interest in the potential of stem cells in regenerative medicine has made well-defined undifferentiated ESC lines widely available as well as undifferentiated iPSCs that are phenotypically and functionally similar to ESCs. In our study we hypothesized that undifferentiated stem cells could be used as a polyvalent vaccine to generate an immune response against a variety of embryonic antigens that are shared by tumor cells and CSC. We found, for the first time, that ESCs or iPSCs were able to induce immune and clinical responses against breast carcinoma. Surprisingly we found that the addition of valproic acid in the therapeutic regimen could induce higher immune and anti-tumoral responses in comparison to the use of ESCs or iPSCs alone.

Material & Methods

We have developed a metastatic 4T1 breast tumor model in BALB/c mice. To verify the embryonic ES-like markers in 4T1 murine TNBC breast cancer cell lines a meta-analysis was performed with the embryonic cell samples (D3 stem cell—GSE51782 annotated with Affymetrix plateform GPL16570) and with integration of different datasets: TNBC cell line 4T1 cultivated in vitro (GSE73296 annotated with Affymetrix plateform GPL6246), TNBC cell line 4T1 xeno-transplanted in mouse model (GSE69006 annotated with Affymetrix plateform GPL6246) and mammary gland samples (GSE14202 annotated with plateform GLP339) (Padovani et al. 2009). For this 4T1 model it was shown by micro-array analysis that transplanted 4T1 in balb/c mice share 1304 different genes with murine ESCs including TRAP1A, TET1, TSLP, FAM169A, ETV5, MOXD1, PHLDA2, CRIP1, ADAMDEC1, NID1, EPCAM, H2-EA-PS, GPA33, IBSP, KANK3, MEST, MMP9, SPRY4, CLDN4, PRSS22, DDAH2, SPRY2, USP11, CTNNAL1, ZFP532, GRB10, CACNG7, ST14, CTH, RCN1, PECAM1, TMEFF1, PPP1R1A, GPR97, KIF2C, BRCA2, SLAIN1, CSRP2, DOCK6, HUNK, RAD51, ESYT3, SKP2, CCL24, SFRP1, HMGB2, ITM2A, ASPN, MSH2, SUGT1, ARHGAP8, etc. All these genes were thus found commonly upregulated in 4T1 and mESC, in comparison to normal murine mammary gland. It was also shown that xenotransplanted 4T1 highly expressed CSC markers such as CD44 compared to cells that were harvested in vitro (39% versus 0.27% of $CD44^{high}CD24^{low}$) (not shown).

In the same manner a whole-genome expression profile analysis was performed on Triple Negative Breast Cancer (TNBC) from patients. To verify the embryonic ES-like markers in patients with TNBC a meta-analysis performed with embryonic cell samples and human breast samples was performed by merging sample data from different datasets: dataset GSE18864 comprising 84 breast cancer samples and annotated with Affymetrix plateform GPL570 (Silver et al. 2010), dataset GSE20437 comprising 42 samples of human normal breast and annotated with affymetrix platform GPL96 (Graham et al. 2010), dataset GSE23402 comprising 42 samples of human embryonic stem cells and induced pluripotent stem cells and annotated with Affymetrix plateform GPL570 (Guenther et al. 2010), dataset of Breast cancer cell lines (Maire et al. 2013) and dataset GSE36953 comprising cell culture samples of TNBC cell lines and annotated with Affymetrix plateform GPL570 (Yotsumoto et al. 2013). A supervised one-way ANOVA analyzed between the 3 grade groups of breast cancer identified 4288 significant genes which allowed to class majority of triple negative breast cancer TNBC grade III with samples of IPS and ES including CDC20, KRT81, NCAPG, MELK, DLGAP5, AURKA, ADAM8, CCNB1, RRM2, QPRT, SLAMF8, EZH2, CENPF, HN1, CENPA, SLC19A1, SLC39A4, CDK1, SEPHS1, GMDS, TUBB, SCRIB, DDX39A, YBX1, MKI67, TKT, WDR1, SKP2, ISG20, NRTN, SEC14L1, GAPDH, ILF2, PSMB2, DHTKD1, TPX2, CCNB2, IL27RA, NADK, H2AFX, MRPS18A, AURKA, MCMI, MCAM, NOP2, KIF23, JMJD4, YIPF3, CDH3, TALDO1, BID, C16orf59, HMMR, BIRC5, ZNF232, RANBP1, CDK1, SHMT2, KIF20A, EPHB4, SPAG5, PPARD, ORC6, TUBB4B, LYZ, TK1, PDXK, NAA10, BAG6, SF3B3, MARCKSL1, MCM3, PSRC1, NUSAP1, etc. All these genes were thus found commonly up regulated in TNBC tumors and hESCs compared to normal human mammary gland.

Results

Result 1 Vaccination with Xenogeneic Embryonic Stem Cells Generates a Immunological and an Anti-Tumoral Response Against Breast Cancer.

Figure 2:
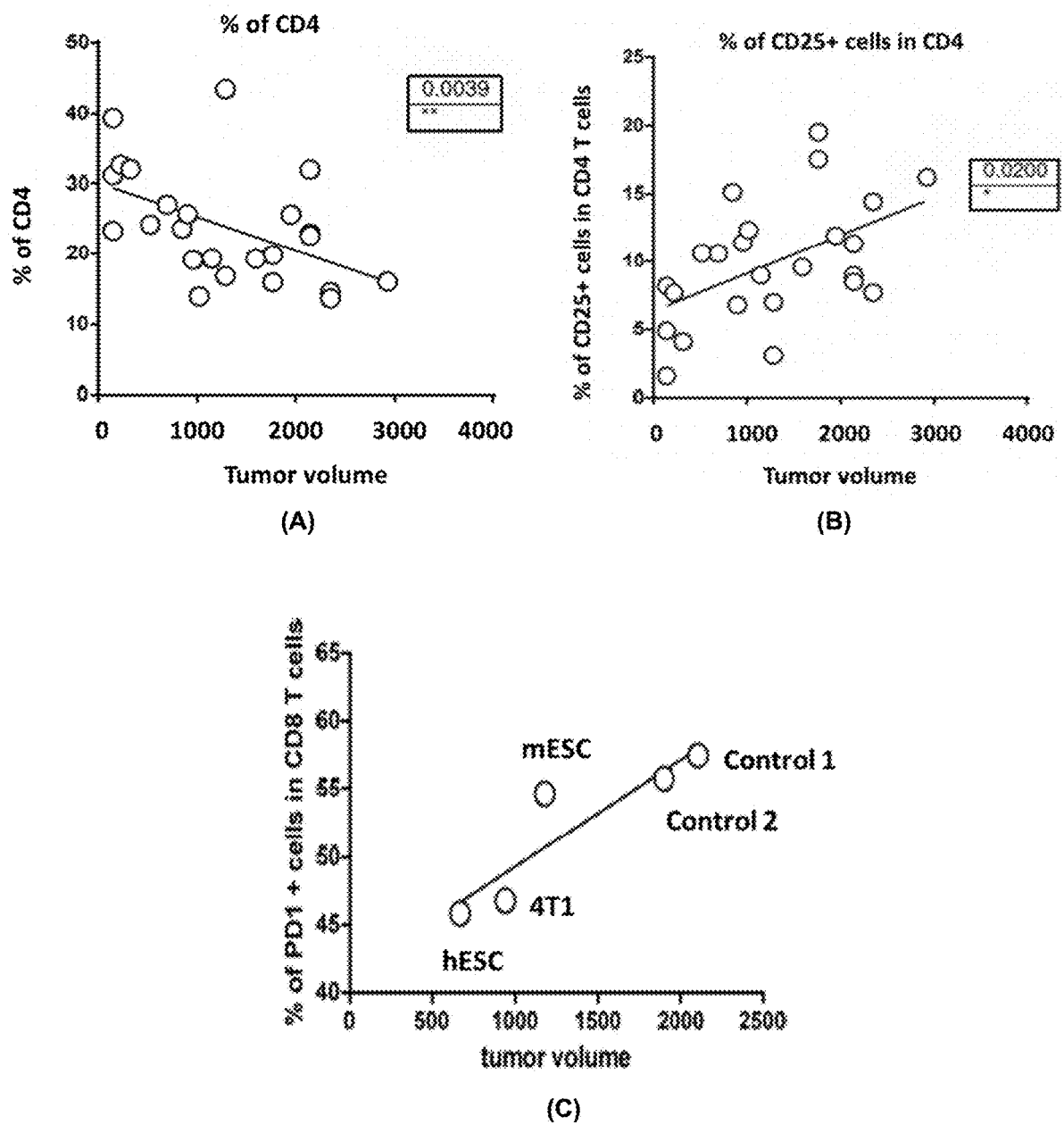
FIG. 2: Immune protection after vaccination. A; Quantification of CD4 positive tumor infiltrating lymphocytes (TIL) by flow cytometry. B; Quantification of CD25 positive regulatory T cells by flow cytometry within the CD4+ TIL. C; Quantification of PD1 regulatory T cells by flow cytometry within the CD8+ T cells regarding the group of mice.

We first investigated whether vaccination with irradiated murine ESCs (mESC), murine induced Pluripotent Stem Cells (murine iPSCs), human embryonic stem cells (hESCs) or 4T1 cells was effective against breast cancer in a syngeneic 4T1 mice model. This vaccination was followed by challenging the mice with two different types of 4T1 cells: the 4T1 cultured normally in DMEM 10% of SVF or 4T1 cells that were growth with additional cytokines such as TGFbeta and TNFalpha in order to generate Cancer Stem Cells (CSC) growing in the form of mammospheres. We discovered that in contrast to the non-vaccinated mice, the mice vaccinated with hESCs, mESCs, murine iPSCS and 4T1 generated consistent cellular immune responses against 4T1 carcinoma that was correlated with a significant reduction of breast tumor volume (p<0.05) (FIG. 1). We found that tumors grew progressively in the PBS-control group whereas, strikingly, immunization with mESC, miPS or hESC resulted in a retardation of tumor growth, with statistically significant differences in the average tumor size in each group compared with PBS group (FIG. 1). We observed a drastic inhibition of tumor growth when mice were challenged with CSC derived −4T1 compared to the mice challenged with 4T1 that were growth under normal condition showing that the vaccination with syngeneic mESC preferentially targets CSCs. To further study the cellular immune mechanism mediating the antitumor effect, we analyzed the phenotype of tumor infiltrating lymphocytes from different groups and quantified the CD4, CD8, CD25 and PD1 subpopulations. The anti-tumoral effect was correlated with 1/an increase of CD4+ TIL that was significantly (p=0.0039) correlated with the tumor size (FIG. 2A), 2/a decrease of the percentage of CD25 positive cells that was inversely correlated with the tumor size (FIG. 2B), 3/a decrease of PD1 positive cells that was more pronounced in mice having better repose to the vaccine regimen (vaccination with hECS, 4T1 or mESC) (FIG. 2C).

Result 2 Vaccination with Xenogeneic Embryonic Stem Cells in Combination with Valproic Acid (VPA) Generates a Higher Anti-Tumoral Response Against Breast Cancer and Inhibits Metastasis Development.

Figure 3:
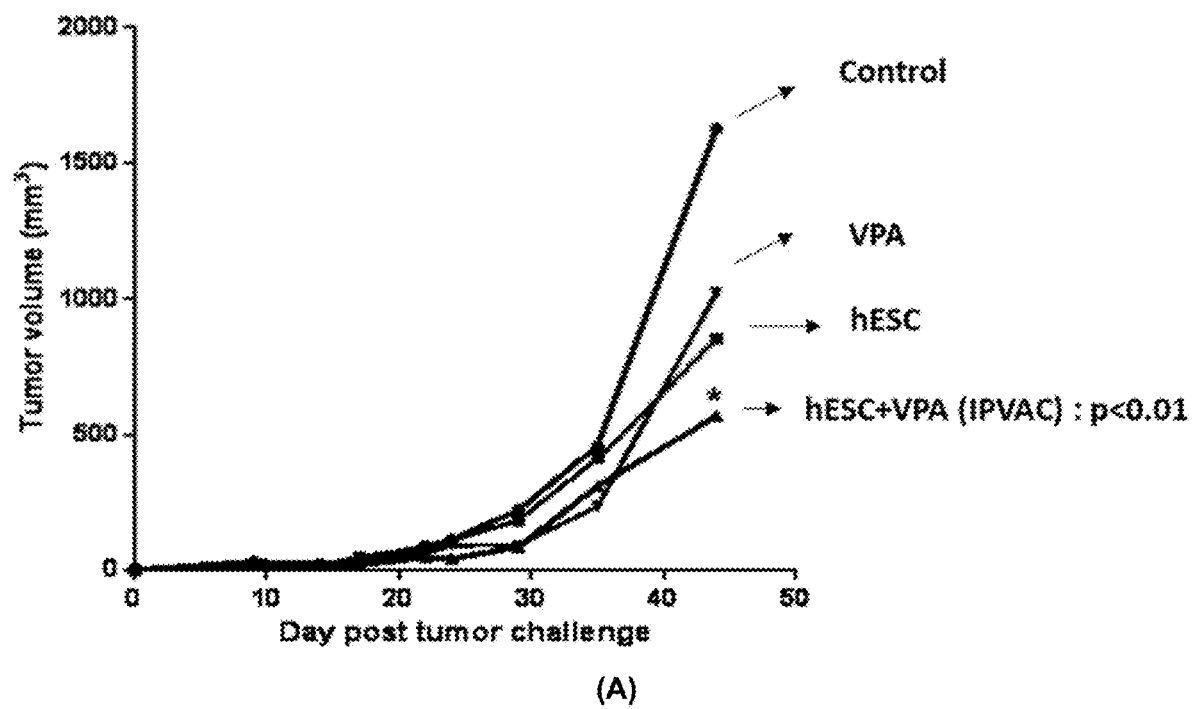
FIG. 3: Vaccination study with hESC combined with VPA on 4T1 mice model. Study design: Mice (n=5 per group) received to boosts of vaccine 7 and 14 days with $10^5$ irradiated cells hESCs with or without VPA. After 14 days $5\times10^4$ 4T1 cells were injected into the mammary fat pad of the mice. A; Tumor volumes for each group: 1/control (PBS), 2/vaccination with hESC 3/vaccination with hESCs combine with VPA, 4/mice receiving only VPA. B: tumors weight at 44 days.
Figure 3:
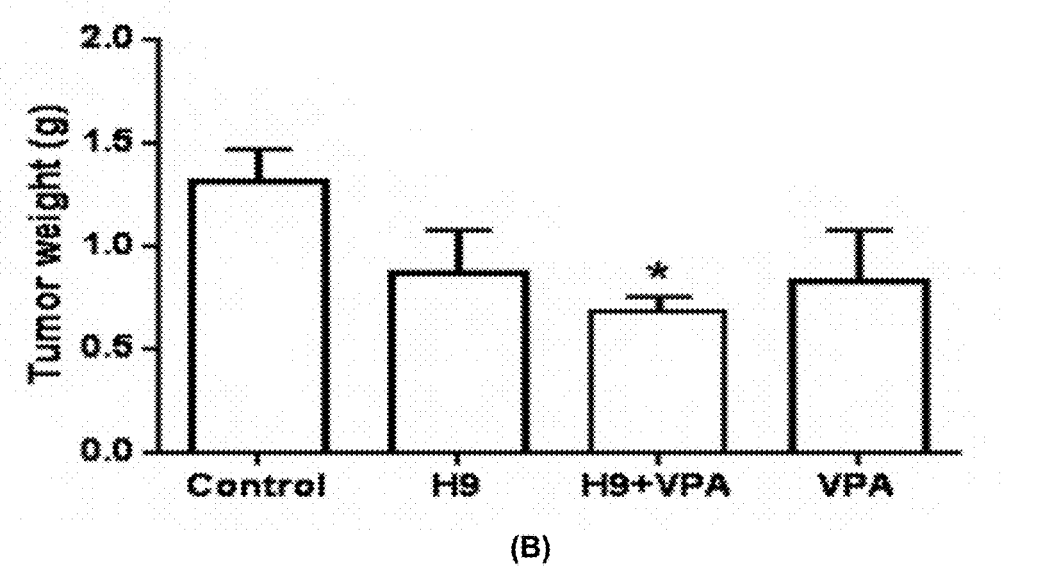
Figure 4A:
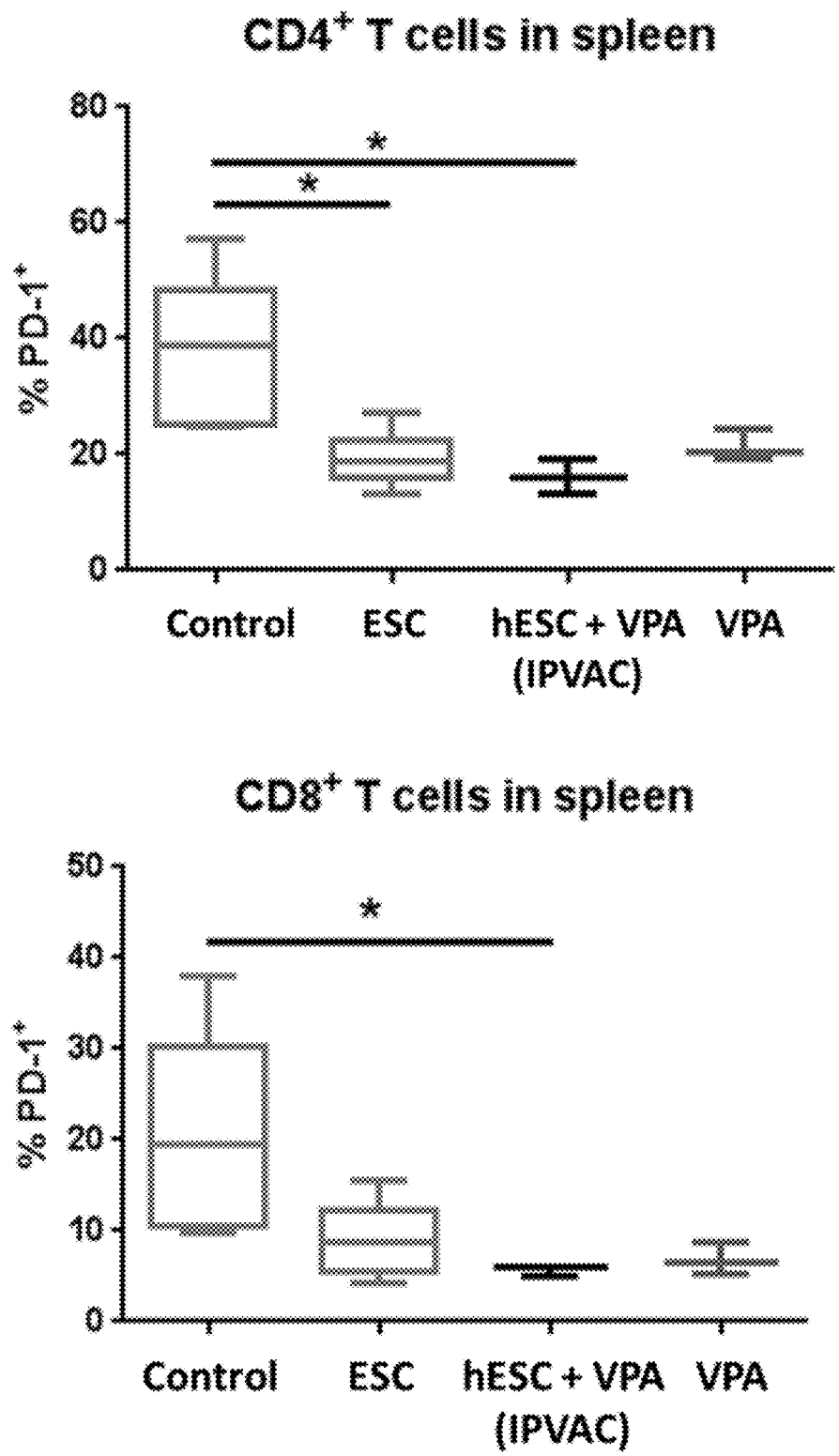
FIG. 4: Immune protection after hESC vaccination and VPA: A; decrease of PD1 cell in the spleen within the CD4 and CD8 populations. B, increase CD4+ and CD8+ T cells in the tumors. C: increase of CD4+ and CD8+ T cells in the spleen
Figure 4B:
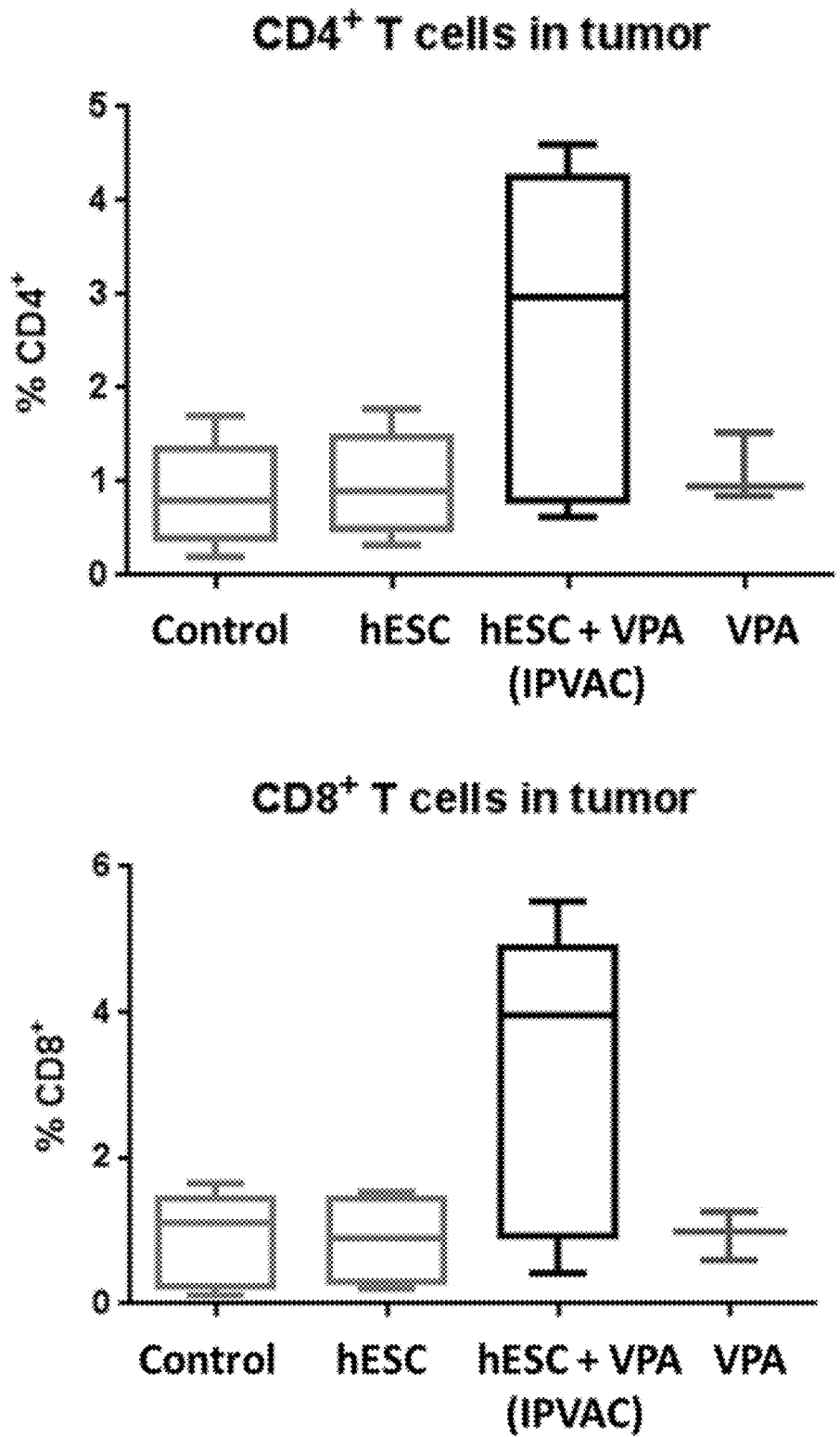
Figure 4C:
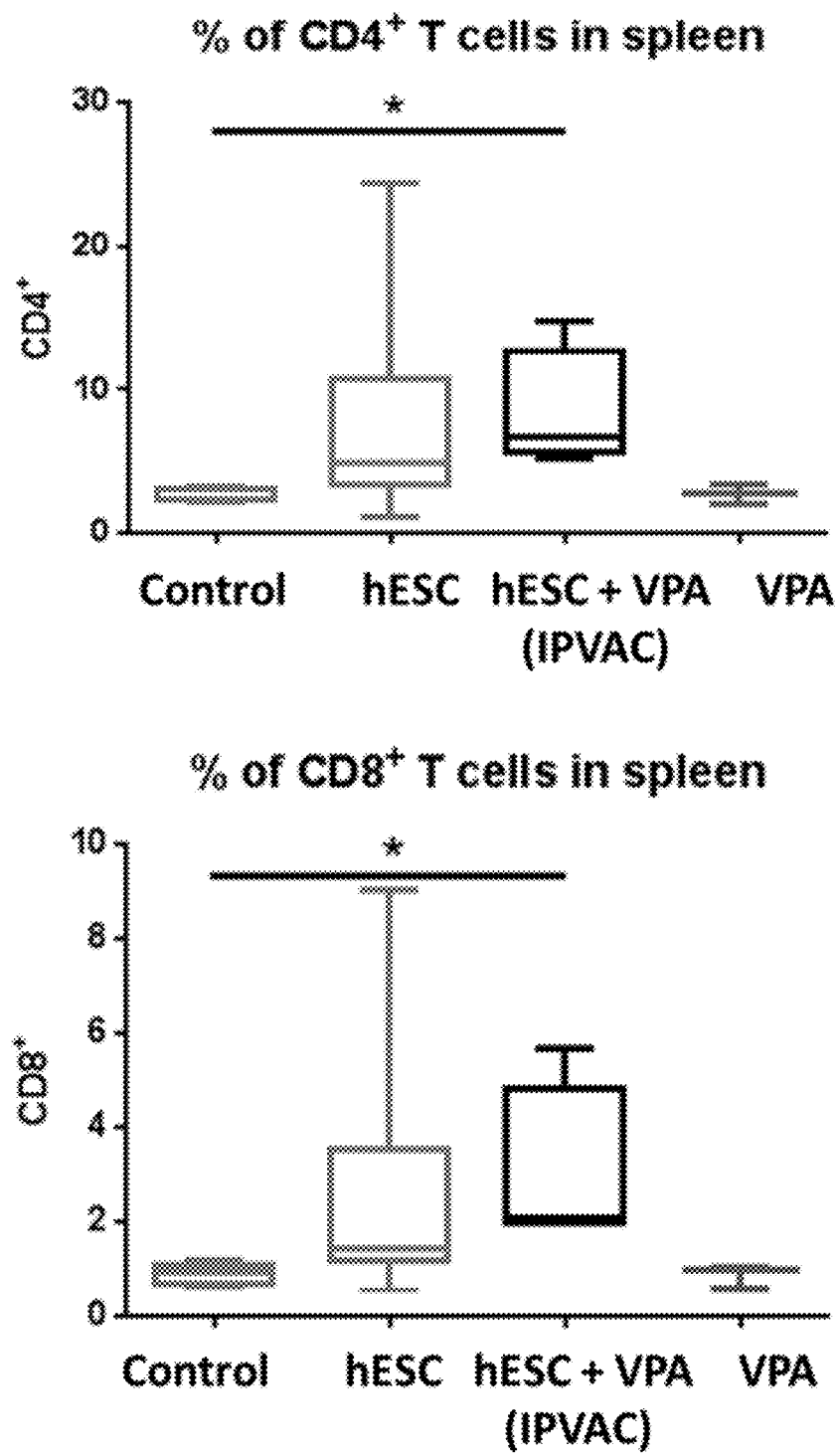
Figure 5:
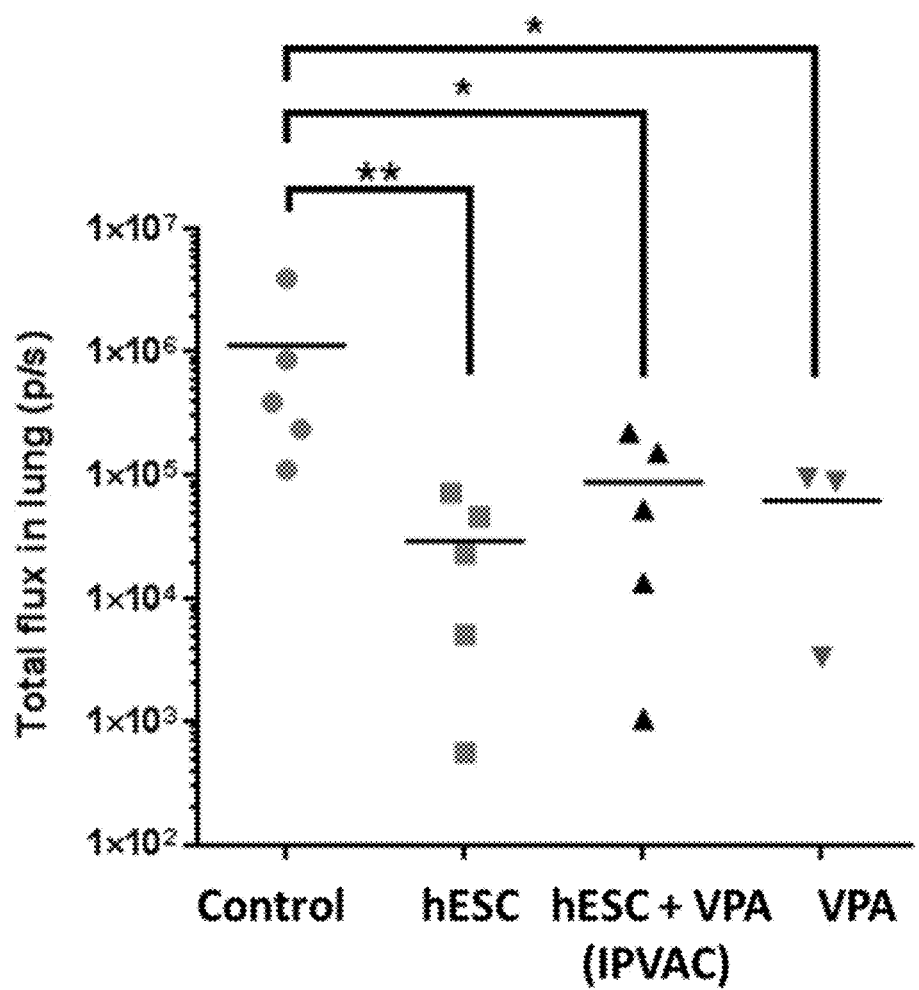
FIG. 5: Quantification of the luciferase reporter gene by the IVIS-Spectrum system on lungs after dissection for each animal of the 4 groups (control, hESC, hESC+VPA, VPA).

To evaluate the metastatic sites in the 4T1 breast models, the 4T1 cells were genetically modified so that they expressed both GFP and luciferase reporter protein (4T1Luc-GFP), enabling their tracking in vivo using bioluminescence imaging (Ivis spectrum) in deeper organs (spleen, lung, bone, liver). The experiment was carried out as previously described but using only irradiated hESCs as the vaccine; 5 mice per group received two boosts of vaccine 7 and 14 days with $10^5$ irradiated hESCs cells with or without VPA at the dose of 0.40 mM in drinking water. After 14 days $5 \times 10^4$ 4T1Luc-GFP cells were injected into the mammary fat pad of the mice. We discovered that in contrast to the non-vaccinated mice, the mice vaccinated with hESCs combined with VPA generated a higher cellular immune responses against 4T1 carcinoma that was correlated with a significant reduction of breast tumor volume (p<0.05) (FIG. 3A,) and reduction of the tumor weight (FIG. 3B). The anti-tumoral response was correlated with a drastic decrease of PD-1 expression on both in CD4+ T cells and CD8+ T cells in the mice receiving hESC and VPA (FIG. 4A). In addition the anti-tumoral response was correlated with a significant increase of the percentage of CD4+ T and CD8+ T cells within the tumor (FIG. 4B) and within the spleen (FIG. 4C) exclusively for the mice having received the combined treatment (hESC and VPA) compared to the control group (PBS). We also found that all mice had significantly reduced lung metastasis mice treated with hESCs vaccine and VPA (FIG. 5). Taken together, these results show that xenogeneic embryonic stem-based vaccination (hESC) with VPA has the strongest efficacy compared to the use of hESC and VPA alone. These results show that xenogeneic embryonic stem-based vaccination could be an efficient treatment to reduce tumor relapse in breast carcinoma.

Example 2

Valproic Acid Modulates the Expression of MHC Class 1 and the Expression of Embryonic Genes The major histocompatibility complex (MHC) is a set of cell surface proteins essential for the acquired immune system to recognize foreign molecules that plays an essential for the acquired immune system. The main function of MHC molecules is to bind to new and foreign antigens and to display them on the cell surface for recognition by the appropriate T-cells: By interacting with CD4 molecules on surfaces of helper T cells, MHC class II mediates establishment of specific immunity called acquired immunity or adaptive immunity. By interacting with CD8 molecules on surfaces of cytotoxic T cells, MHC class I mediates destruction of infected or malignant host cells.

Immune tolerance is an important means by which growing tumors, which have mutated proteins and altered antigen expression, prevent elimination by the host immune system. Tumor immune tolerance can be explain in part by the absent of β2-m on the cell surface and or the absence of MHC class I on tumor cell. It was shown that VPA is able to increase the expression of MHC class I on 4T1 cells at dose between 0.2 mM to 2 mM.

The expression of MHC class I on 4T1 and 4T1 mammosphere (CSC induced by the treatment by TNFa and TGFb) increases by 2 to 3 fold after 24 hr to 72 hr of exposure with 2 mM of VPA.

In particular, it was shown that VPA is able to increase the expression of HLA ABC MHC class I on iPSCs (63% versus 92%) and the expression of pluripotent markers such as SSEA4 and Tra1-60 (55% versus 72%) at the dose of 0.5 mM.

Those markers were decreased after ENU exposure (60 days of treatment), and were restored when cells were treatment with 0.5 mM of VPA (28% to 92% of HLA ABC positive iPSCs-ENU and iPSCs respectively) and (48% to 69% of SSEA4/Tra-1-60 positive iPSCs-ENU and iPSCs respectively).

Figure 6A:
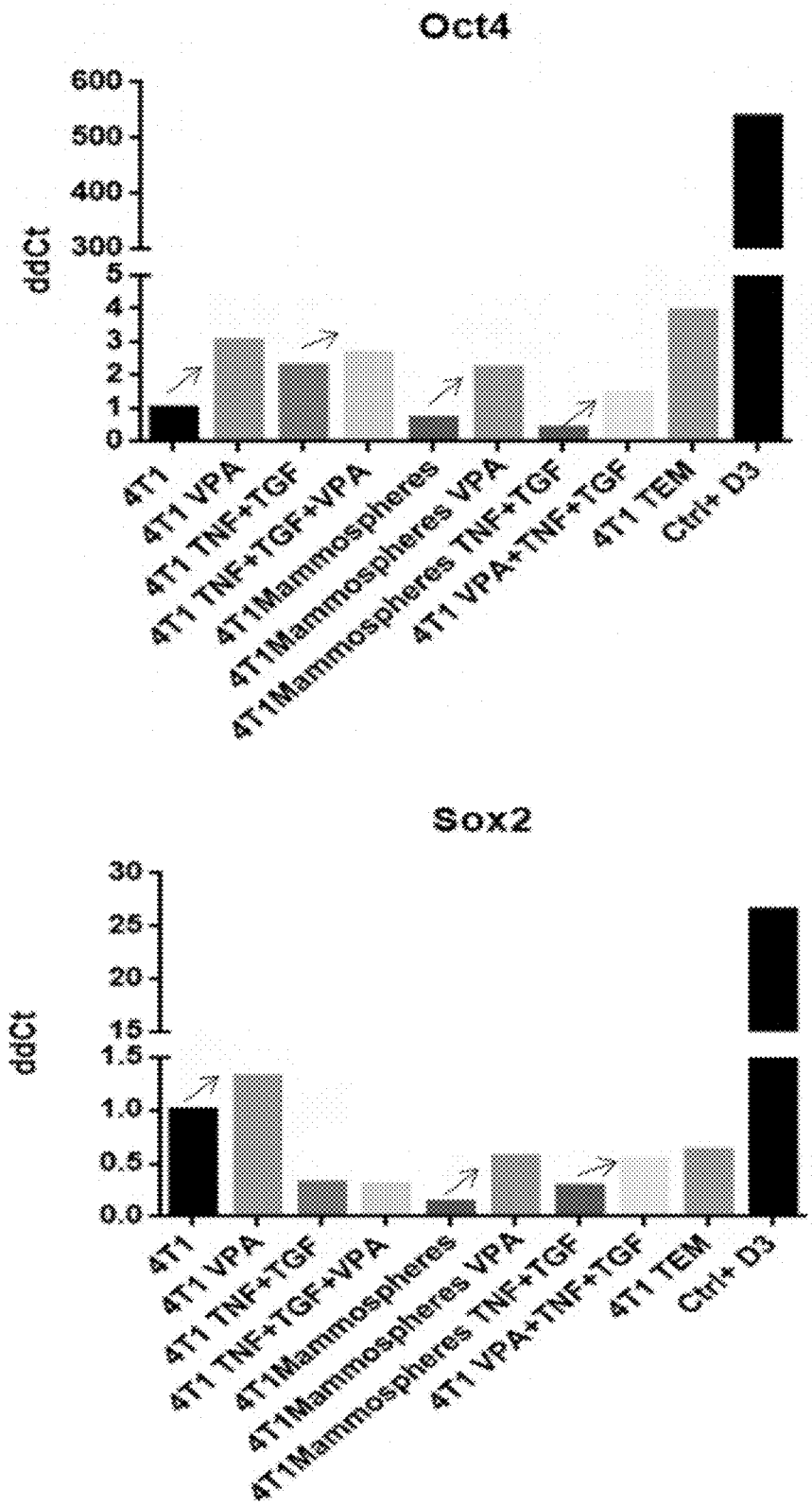
FIG. 6: Expression of puripotent genes (Oct 4 (FIG. 6A), Sox2 (6.B) and Nanog (FIG. 6C)) by real time PCR on 4T1 cells and 4T1 CSC (mammospheres) treated with 0.5 mM of VPA for 5 days.
Figure 6B:
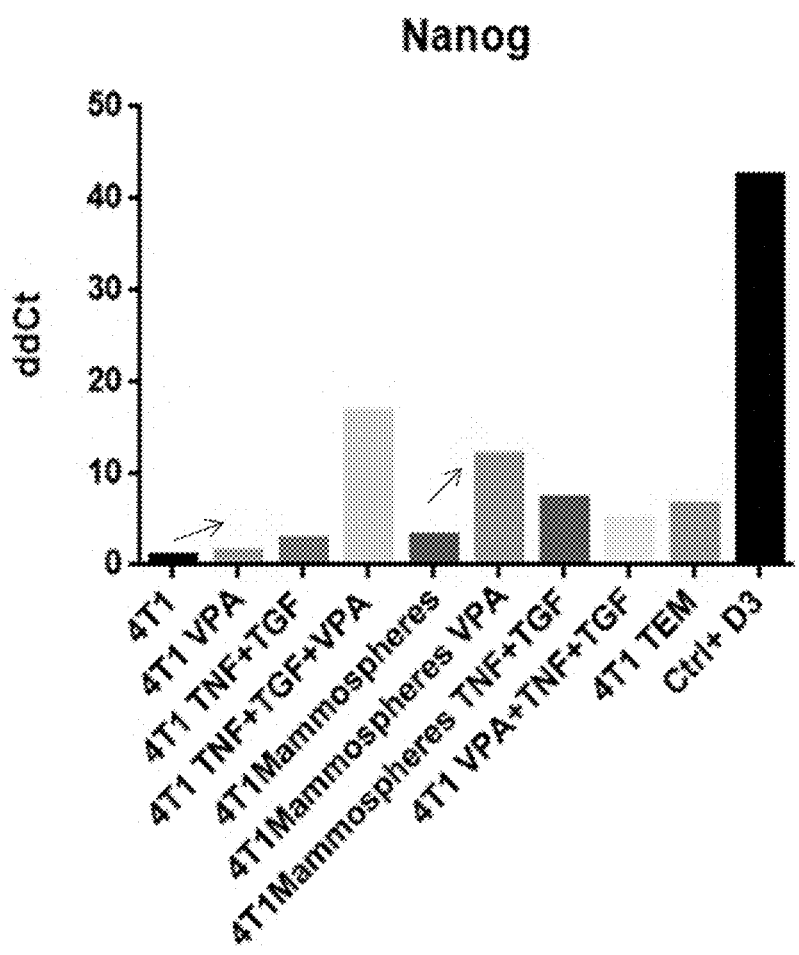
Figure 7:
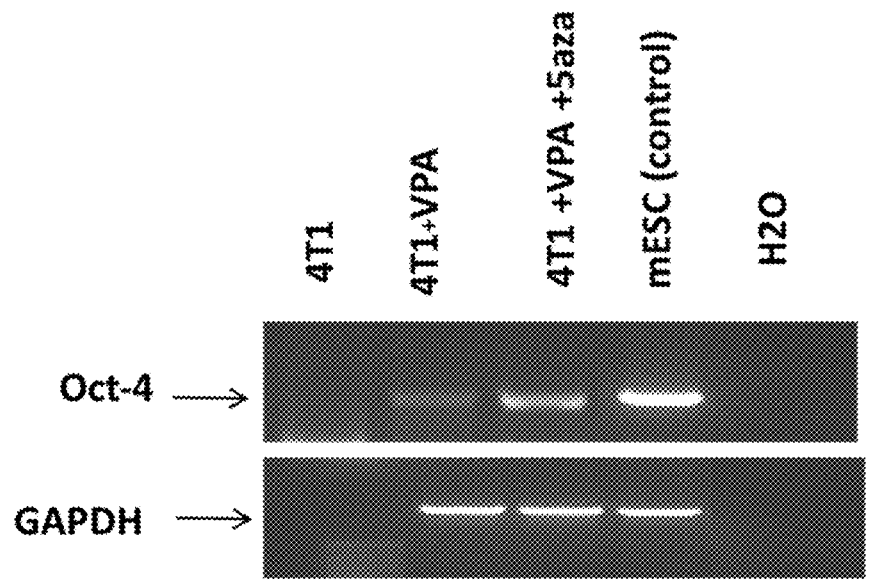
FIG. 7: Expression of Oct4 in 4T1 treated with VPA and 5Aza by RT PCR (FIG. 7A) and real time PCR (FIG. 7B).
Figure 7:
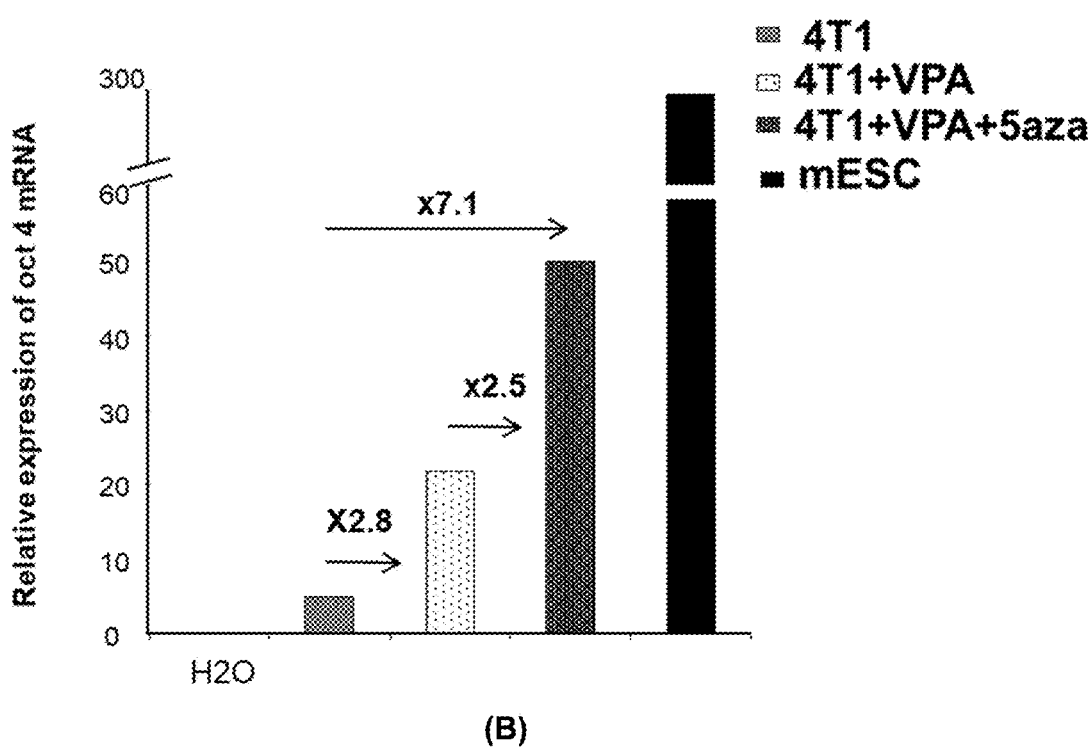

HDAC inhibitors as VPA can selectively alter gene transcription, in part, by chromatin remodeling and by changes in the structure of proteins in transcription factor. It was studied whether VPA can modulate the expression of pluripotent gene in breast tumor cells. For this purpose we have treated 4T1 and 4T1 mammospheres (CSC induced by the treatment by TNFa and TGFb) with 1 mM to 2 mM of VPA. In all cases VPA have increased by 2 to 3 fold the expression of three different important transcriptional factors that are highly expressed in ESC or iPSC such as Oct 4, Sox2 and Nanog (FIG. 6). Importantly, an important synergic effect of these transcriptional factors expression was shown when tumor cells were treated with the combination of VPA and 5-Azacytidine (5aza) when used at doses that inhibits DNA methyltransferase, causing hypomethylation of DNA. In particular a 7 fold increase of oct-4 transcript was shown when 4T1 cells were treated with VPA and 5aza (FIGS. 7 A and B).

Example 3

Inducing DNA Damage and DNA Repair Errors by Genomic Instability in iPSCs Exposed to Mutagens Drug Such as N-Ethyl-N-Nitrosourea (ENU)

Ethyl-N-Nitrosurea (ENU) is a mutagenic alkylating agent which creates base transversions but also single point mutations and double strand DNA breaks (DSB).

It was possible to confirm that ENU allows DNA damage in iPSC.

The amount of phosphorylated gamma-H2AX attracted to the sites of DSB present in the cells was evaluated. In this experiment, iPSC were detached from stromal cultures by the use of collagenase and treated in vitro with ENU at indicated concentrations (50 µg/ml) and times, followed by Western blot analyses using an anti-phospho-gamma H2AX antibody. An increase of gamma-H2AX levels seen as early time points as 2 minutes-10 minutes was shown, followed by return to basal levels.

A protocol was designed, to induce genomic instability in iPSC by a sequential treatment of IPSC with ENU in order to accumulate DNA repair errors during extensive proliferation. Cells were treated for 60 days with daily medium changes with daily addition of ENU at a concentration of 10 µg/ml. VPA was added during culture.

At day+61, iPSCs are evaluated the genomic consequence of mutagenesis procedure in iPSC by Karyotype, and RNA sequencing, CGH arrays, exome sequencing, WGS. Genomic alterations accumulated in cultured iPSC are compared to iPSC not treated with ENU.

Figure 8:
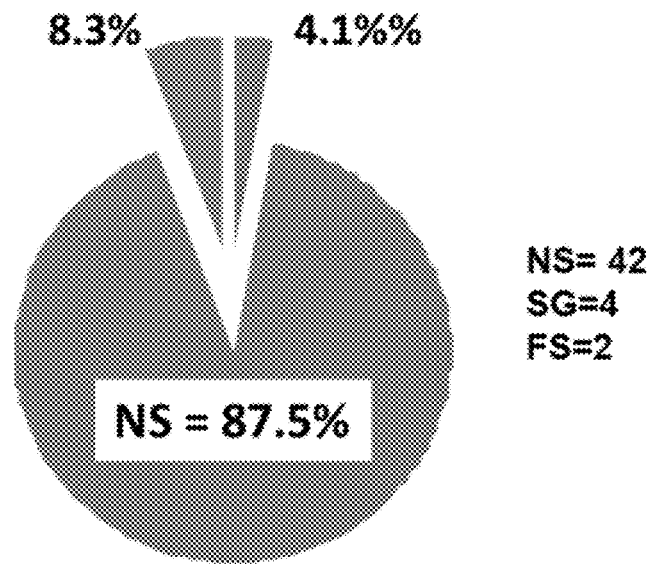
FIG. 8: Detection by exome sequencing of genetic variants altering protein sequences of neoantignes in iPSC treated or not by ENU. Quantification of variants in ENU-treated iPSC and none treated-iPSCs. (NS=Non Synonymous, FS=frameshift, SG=Stop Gained).
Figure 8:
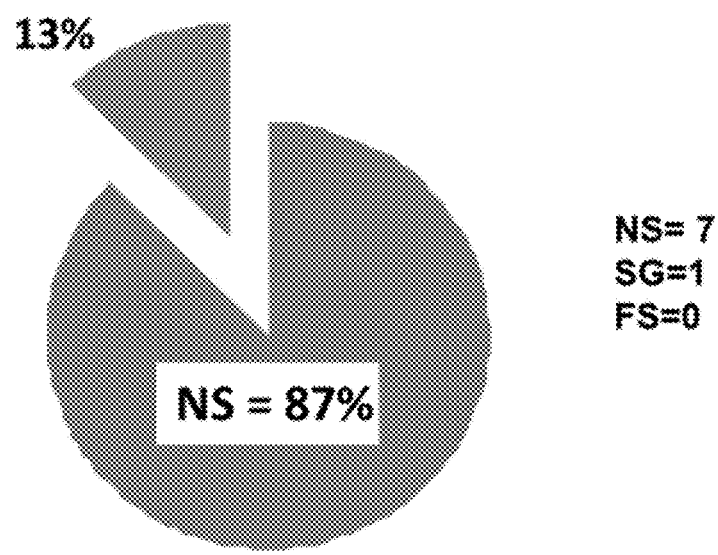
Figure 9:
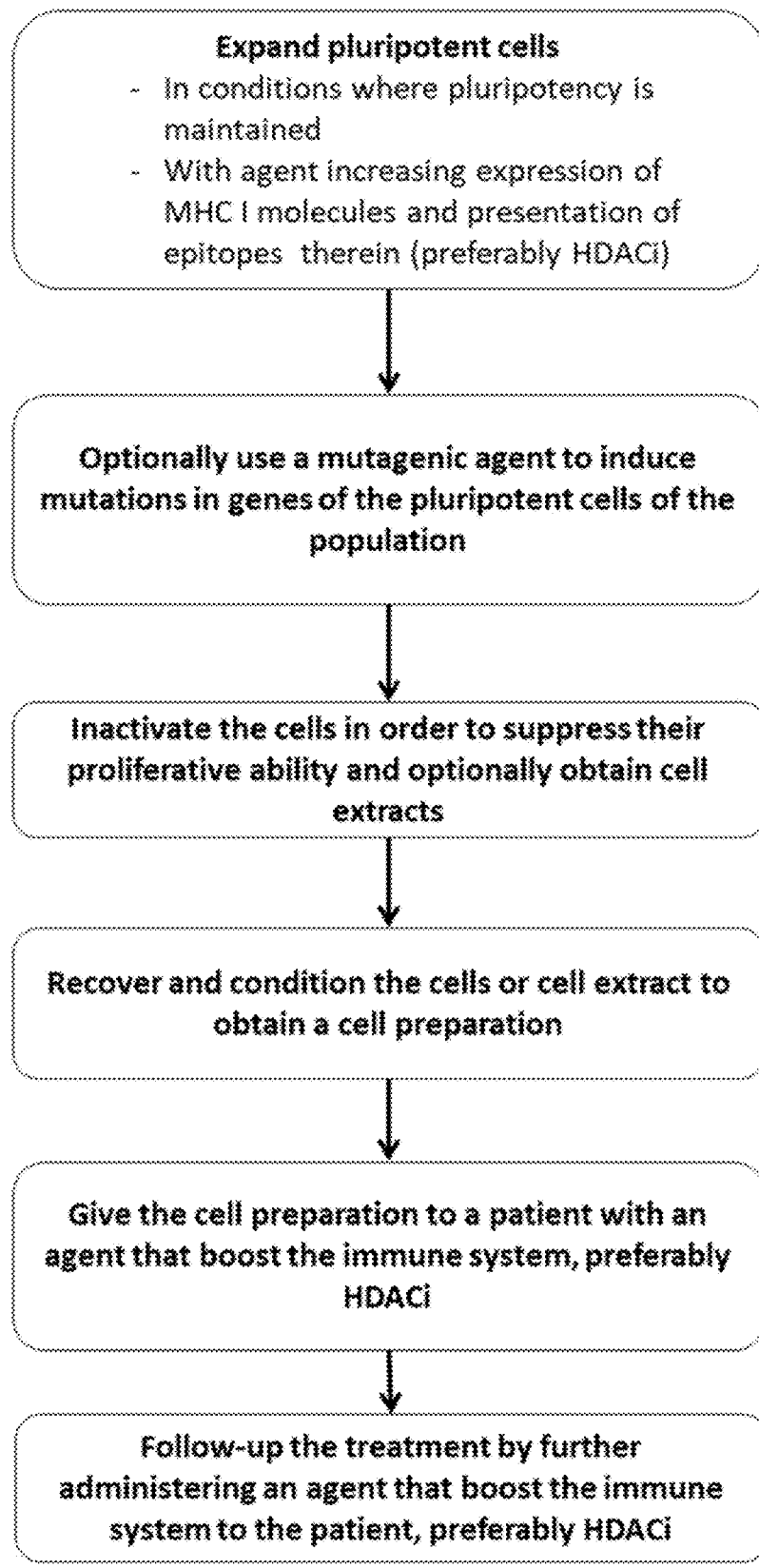
FIG. 9: schematic representation of a process according to the invention.

After ENU exposition, mutated iPSC were maintained and expanded in culture with VPA. CGH arrays and exome sequencing are performed sequentially at different passages to confirm the genocopy of the somatic mutation prevalence in ENU-iPSC during their expansion. Phenotype of iPSCs is performed by assessing pluripotency Pluritest and expression of Oct4, Sox2, Nanog, Tra-1 60, SSEA4. We found that replication rate and population doubling are similar to iPSC without ENU exposition.

iPSC were treated with 10 µg/ml of ENU and performed a exome sequencing for the detection of mutated neo antigens. 48 alterations in ENU treated-iPSC where found compared to 8 alterations in iPSCs without ENU (FIG. 8). These loci were merged with cBioPortal program allowing access to cancer genomics data sets from human tumor samples from different cancer studies. Using cBioPortal program it was shown that more than 10 to 75% of these alterations were found also deregulated in carcinoma (pancreas, lung prostate . . . ). For all exome sequencing we estimate the depth of coverage of 30 to 400 reads for all mutations that can be detected in ENU-treated iPSC.

Example 4

Haploinsufficiency for BRCA1 Leads to DNA Repair Alteration and Genomic Instability with CNVs Accumulation in iPSC During Culture Alteration of BRCA1/2 is involved in Hereditary Breast and Ovarian Cancer (HBOC) syndrome. BReast CAncer1 (BRCA1) is a tumor-suppressor gene and plays a pivotal role in the maintenance of genomic stability by controlling DNA repair in homologous recombination, double-strand break repair, S-phase and G2/M, spindle checkpoints, and in centrosomal regulation.

A fibroblast harboring a deletion of exon 17 in BRCA1 was reprogrammed with Sendai viruses containing Oct3/4, Sox2, Klf4, and cMyc (CytoTune®-iPS Sendai Reprogramming Kit, Life technologies). Cells were cultured in human pluripotent stem cell medium (hPSC medium) based on DMEM/F12 supplemented with 20% Knock Out Serum Replacer, 1 mM L-glutamine, 1% penicillin/streptomycin, 100 µM 2-mercaptoethanol (Life technologies) and 12.5 ng/ml basic FGF (Miltenyi Biotech). At day 26, fully reprogrammed colonies were manually picked based on their morphology and pluripotency markers by FACS analysis, Q RT-PCR of Nanog, Oct4 Sox2, teratoma formation in NOD-SCID mice and Pluritest. Karyotype was normal.

The levels and activity of the DNA Damage Response (DDR) in normal (WT) and BRCA1+/−iPSCs were compared. Gamma H2AX foci was determined by immunofluorescence in proliferating iPSC after irradiation or ENU exposition. IPSC BRCA1+/−exhibited significantly higher levels of phosphorylated ATM/ATR substrates as well as gamma H2AX recruitment to DNA compared with normal WT-iPSC, indicating that proliferating IPSC BRCA1+/− suffer increased DNA damage compared with WT-IPSC.

Since iPSC BRCA1+/−displayed increased levels of DDR at early passages, it was examined whether this might be associated with accumulation of genomic alterations during iterative passages and proliferation.

CGH array in proliferating pluripotent stem cells was analyzed after prolonged passaging of iPSC in medium supplemented with HDACi (VPA). For this purpose, Agilent CGHarray experiments were performed on DNA from IPSCs samples with the Roche-Nimbelgen aCGH platform. Signal extraction and genomic intervals were identified with Agilent cytogenomics and Nexus Roche-Nimbelgen softwares on HG18 of human genome. Gene loci were converted on HG19 coordinates with Roche-Nimbelgen annotation files (Genes_July_2010_hg19, Roche-Nimbelgen website). European Copy number variations (CNV) polymorphism were eliminated from experiments with scandb database (Gamazon et al. 2010). Array CGH CNV ratios were drawn as heatmap with MEV version 4.9.0 standalone software (red: gain, green: loss and dark zero) (Saeed et al. 2003). Gene loci found affected in cell of origin were subtracted from gene loci affected in respective IPSCs sample. Resulting filtered CNV specific of each iPSCs were merged COSMIC census database (Futreal et al. 2004). Genomic Circosplot on HG19 was performed with cancer genes found affected in each IPSCs after filtration. This genomic draw was performed with OmicCircos R-package in R environment version 3.0.2 (Hu et al. 2014).

It was shown that culture of iPSC BRCA1+/−(>100 days) leads at late passages to an accumulation of genomic abnormalities concomitant with increased genomic instability without ENU exposition. Karyotype at late passage is normal. Agilent aCGH experiments were performed on DNA extract from iPSC cells and from their respective cell of origin. Genomic mapping of intervals affected during these pluripotency inductions showed that BRCA1+/−IPSC was affected by an important number of gene loci affected as compared to WT one. After CNV European polymorphism filtration on WT iPSC only 58 gene loci were still found affected (polymorphism represent 1.69% of the total loci affected), similarly on BRCA1-/+iPSC 5273 gene loci were still found affected after polymorphism filtration. Majority of gene loci affected in BRCA1+/−iPSC concerned gain of DNA.

Among these gene loci affected by genomic instability some of them are known as driver cancer gene in census COSMIC database. WT iPSCs showed only one cancer gene locus affected in aCGH (CDK4). BRCA1-/+IPSC is affected by alterations concerning 131 cancer gene loci and among them 11 genes are known to be affected in breast cancer: MSH2, SMARCD1, TBX3, CDH1, TP53, ERBB2, CDK12, BRCA1, PPP2R1A, AKT2, EP300. These alterations were found particularly over-represented on small chromosomes 19 and 17: chromosome 17 which is the chromosome of BRCA1 gene loci.

All together the majority of iPSC BRCA1+/−exhibited a higher amount of indels (deletion or amplification) compared in WT-IPSC. A rate of 8% of CNVs on 5273 genes was identify and validated. Bioinformatic analysis revealed the expression of 131 genes identified in cosmic data base to be involved in cancer development, essentially in leukemias, epithelial tumors and in mesenchymal tumor cells. Some altered genes are similarly observed in breast and ovarian cancers.

Replication rate, pluripotency gene (Pluritest, cell surface markers) and MHC I are maintained and stable during all time of culture in presence of VPA.

In conclusion deletion or inactivation of DNA repair related genes such as BRCA-1 allow to induce genomic instability leading to generate multiple CNV, indels and mutations associated to MHC I.

Example 5

N-Ethyl-N-Nitrosourea (ENU) Increases the Load of Mutated Neo Antigens in CML-iPSCs Characterization of iPSC generated from leukemic blood cells of a patient with Philadelphia-positive chronic myeloid leukemia (CML). iPSC were generated by the use of Sendai-virus mediated transfer of pluripotency genes Oct4, c-Myc, Klf4 and Sox2. Cells with pluripotent iPSC morphology were amplified and characterized using cell surface pluripotrency markers (Tra-1-60 and SSEA4) as well as by their ability to generated teratoma after intramuscular injection into NSG mice. These iPSC harbored Philadelphia chromosome characteristics of CML. CML iPSc were exposed to ENU during 60 days. Cell derivatives blast colonies from CML-IPS treated by ENU were compared to IPSC not treated with ENU.

DNA of CML iPSC was analyzed by CGH array Several genomic aberrations were observed in blast-colonies derived drom ENU-treated iPSC with detection of loss of heterogeneity among genomic aberrations selected by ENU pressure on CML IPSC (CB32 These included copy number variations CNVs which comprised 332 gene loci). After filtration on European Caucasian genomic polymorphism database 255 gene loci were still present in these genomic aberrations. Majority of the genomic abnormalities included loss of genomic DNA (71%) with loss of heterozygosity (23%). Matching these genomic aberrations with transcription factor database, cancer gene database and pluripotency gene database allowed to observe that these important deregulated actors are principally affected on chromosomes 7, 8, 15, Y, and X. A Circosplot also allowed to determine that majority of these abnormalities implicated transcription factors such as MESP implicated in mesodermal cell migration and IKZF1. Some pluripotency genes were affected as well as some cancer genes like IDH2, NCOA2, IKZF1, BLM which have been already described to be involved in Ph1-positive leukemias, suggesting the relevance of the abnormalities generated by ENU-induced mutagenesis.

This analysis shows that several gene alterations such as gains and losses and several of the abnormalities identified were found to be cancer genes identified in Cosmic database. The comparison of the abnormalities identified in the ENU-iPSC allowed to reproduce the aggressive acute leukemia phase abnormalities already identified in CML patients in acute leukemia phase, suggesting that ENU-treated CML iPSC is a unique tool to reproduce in vitro these genomic abnormalities in this specific cancer.

Throughout this application, various references describe the state of the art to which this invention pertains. The disclosures of these references are hereby incorporated by reference into the present disclosure.

REFERENCES

Graham, K., A. de las Morenas, A. Tripathi, C. King, M. Kavanah, J. Mendez, M. Stone, et al. 2010. «Gene Expression in Histologically Normal Epithelium from Breast Cancer Patients and from Cancer-Free Prophylactic Mastectomy Patients Shares a Similar Profile». British Journal of Cancer 102 (8): 1284-93. doi:10.1038/sj.bjc.6605576.

Guenther, Matthew G., Garrett M. Frampton, Frank Soldner, Dirk Hockemeyer, Maya Mitalipova, Rudolf Jaenisch, et Richard A. Young. 2010. «Chromatin Structure and Gene Expression Programs of Human Embryonic and Induced Pluripotent Stem Cells». Cell Stem Cell 7 (2): 249-57. doi:10.1016/j.stem.2010.06.015.

Maire, Virginie, Fariba Némati, Marion Richardson, Anne Vincent-Salomon, Bruno Tesson, Guillem Rigaill, Eléonore Gravier, et al. 2013. «Polo-like Kinase 1: A Potential Therapeutic Option in Combination with Conventional Chemotherapy for the Management of Patients with Triple-Negative Breast Cancer». Cancer Research 73 (2): 813-23. doi: 10.1158/0008-5472. CAN-12-2633.

Padovani, Michela, Jackie A. Lavigne, Gadisetti V. R. Chandramouli, Susan N. Perkins, J. Carl Barrett, Stephen D. Hursting, L. Michelle Bennett, et David Berrigan. 2009.«Distinct Effects of Calorie Restriction and Exercise on Mammary Gland Gene Expression in C57BL/6 Mice». Cancer Prevention Research (Philadelphia, Pa.) 2 (12): 1076-87. doi: 10.1158/1940-6207. CAPR-09-0034.

Silver, Daniel P., Andrea L. Richardson, Aron C. Eklund, Zhigang C. Wang, Zoltan Szallasi, Qiyuan Li, Nicolai Juul, et al. 2010. «Efficacy of Neoadjuvant Cisplatin in Triple-Negative Breast Cancer». Journal of Clinical Oncology: Official Journal of the American Society of Clinical Oncology 28 (7): 1145-53. doi:10.1200/JCO.2009.22.4725.

Yotsumoto, Fusanori, Eriko Tokunaga, Eiji Oki, Yoshihiko Maehara, Hiromi Yamada, Kyoko Nakajima, Sung Ouk Nam, et al. 2013. «Molecular Hierarchy of Heparin-Binding EGF-like Growth Factor-Regulated Angiogenesis in Triple-Negative Breast Cancer». Molecular Cancer Research: MCR 11 (5): 506-17. doi:10.1158/1541-7786.MCR-12-0428.

Futreal, P. Andrew, Lachlan Coin, Mhairi Marshall, Thomas Down, Timothy Hubbard, Richard Wooster, Nazneen Rahman, et Michael R. Stratton. 2004. «A Census of Human Cancer Genes». Nature Reviews. Cancer 4 (3): 177-83. doi:10.1038/nrc1299.

Gamazon, Eric R., Wei Zhang, Anuar Konkashbaev, Shiwei Duan, Emily O. Kistner, Dan L. Nicolae, M. Eileen Dolan, et Nancy J. Cox. 2010. «SCAN: SNP and Copy Number Annotation». Bioinformatics (Oxford, England) 26 (2): 259-62. doi:10.1093/bioinformatics/btp644.

Hu, Ying, Chunhua Yan, Chih-Hao Hsu, Qing-Rong Chen, Kelvin Niu, George A. Komatsoulis, et Daoud Meerzaman. 2014. «OmicCircos: A Simple-to-Use R Package for the Circular Visualization of Multidimensional Omics Data». Cancer Informatics 13: 13-20. doi:10.4137/CIN.S13495.

Saeed, A. I., V. Sharov, J. White, J. Li, W. Liang, N. Bhagabati, J. Braisted, et al. 2003.

«TM4: A Free, Open-Source System for Microarray Data Management and Analysis». BioTechniques 34 (2): 374-78.

Loek J. Eggermont, Leonie E. Paulis, Jurjen Tel, Carl G. Figdor et al 2014 Trends in Biotechnology, 2014. Towards efficient cancer immunotherapy: advances in developing artificial antigen-presenting cells. Adham S. Bear, Conrad R. Cruz, and Aaron E. Foster et al, 2011. T Cells as Vehicles for Cancer Vaccination. J Biomed Biotechnol. 2011; 2011:417403

Cornelis J. M. Melief, Thorbald van Hall, Ramon Arens, Ferry Ossendorp, and Sjoerd H. van der Burg, Therapeutic cancer vaccinesJ Clin Invest. 2015; 125(9):3401-3412

Oluseun Adewumi, Behrouz Aflatoonian, Lars Ahrlund-Richter, Michal Amit, Peter W Andrews, Gemma Beighton, Paul A Bello, Nissim Benvenisty, Lorraine S Berry, Simon Bevan, Barak Blum, Justin Brooking, Characterization of human embryonic stem cell lines by the International Stem Cell Initiative, Nature Biotechnology 25, 803-816 (2007)

Franz-Josef Muller, Bernhard M Schuldt, Roy Williams, Dylan Mason, Gulsah Altun, Eirini P Papapetrou, Sandra Danner, Johanna E Goldmann, Arne Herbst, Nils O Schmidt, Josef B Aldenhoff, Louise C Laurent & Jeanne F Loring A bioinformatic assay for pluripotency in human cells; Nature Methods 8, 315-317 (2011)

Shi Y and al, Nat Rev Drug Discov. 2017 February; 16(2): 115-130.

Chen K G and al Human pluripotent stem cell culture: considerations for maintenance, expansion, and therapeutics. Cell Stem Cell. 2014 Jan. 2; 14(1):13-26

Hussein S M and al, Copy number variation and selection during reprogramming to pluripotency. Nature. 2011 Mar. 3; 471(7336):58-62.

Hussein S M and al, Genome damage in induced pluripotent stem cells: assessing the mechanisms and their consequences. Bioessays. 2013 March; 35(3):152-62.

Wu, Z et al, Adeno-associated virus serotypes: vector toolkit for human gene therapy. Mol Ther 2006; 14:316-27

Choi, V W et al, Effects of adeno-associated virus DNA hairpin structure on recombination. J Virol 2005; 79:6801-07

Graham et al., A new technique for the assay of infectivity of human adenovirus 5 DNA (1978) Virology 52: 456-457

Wigler et al., (1979) Proc. Natl. Acad. Sci. U.S.A. 76 1373-1376 and Current Protocols in Molecular Biology Vol. 1, Wiley Inter-Science, Supplement 14, Unit 9.1.1-9.1.9 (1990)

Lindor et al, 2008 Journal of the National Cancer Institute Monographs, No. 38, Concise Handbook of Familial Cancer Susceptibility Syndromes, Second Edition Chateauvieux et al, J. Biomed. Biotechnol, 2010, pii: 479364. doi: 10.1155/2010/479364

Nicholas P. Restifo, Mark E. Dudley and Steven A. Rosenberg ("Adoptive immunotherapy for cancer: harnessing the T cell response, Nature Reviews Immunology, Volume 12, April 2012

Teifel et al., (1995) Biotechniques 19: 79-80,

Albrecht et al., (1996) Ann. Hematol. 72: 73-79

Holmen et al., (1995) In Vitro Cell Dev. Biol. Anim. 31: 347-351

Remy et al., (1994) Bioconjug. Chem. 5: 647-654

Le Bolc'h et al., (1995) Tetrahedron Lett. 36: 6681-6684

Loeffler et al., (1993) Meth. Enzymol, 217: 599-618

Strauss (1996) Meth. Mol. Biol. 54: 307-327

U.S. Pat. Nos. 5,240,840, 4,806,476, 5,298,429, and 5,396,767

Fournier (1981) Proc. Natl. Acad. Sci. U.S.A. 78: 6349-6353

Lambert et al., (1991) Proc. Natl. Acad. Sci. U.S.A. 88: 5907-59

Marchion D C et al J Cell Biochem. 2004 May 15; 92(2): 223-37.

Valente et al 2014 J Med Chem. 2014 Jul. 24; 57(14):6259-65 and

Valente et al 2014 Expert Opin Ther Pat. 2014 April; 24(4):401-15.

Leoni et al Expert Opin Ther Pat. 2016; 26(2):149-73

Ja et al 2003

Diermayr et al Blood Cancer J. 2012 May; 2(5):e69

Moffat D et al J Med Chem. 2010 Dec. 23; 53(24):8663-78

Banerji et al Clin Cancer Res. 2012 May 1; 18(9):2687-94

Lin et al 2012).

Kaminskas et al Org Biomol Chem. 2004 Sep. 21; 2(18): 2578-84.

Estey et al Leukemia. 2013 September; 27(9):1803-12.

Kantarjian et al Blood. 2007 Jan. 1; 109(1):52-7

Agnew Chem Intl. Ed. Engl. 33:183-186 (1994)

Pardoll, Nature Reviews Cancer 12: 252-264, 2012

Brignone et al., 2007, J. Immunol. 179:4202-4211

Loo et al., 2012, Clin. Cancer Res. July 15 (18) 3834

Fourcade et al., 2010, J. Exp. Med. 207:2175-86

Sakuishi et al., 2010, J. Exp. Med. 207:2187-94

Rosenberg et al., N Engl J Med. 1988 Dec. 22; 319(25): 1676-80.

Rosenberg Cancer Treat Rev. 1989 June; 16 Suppl A:115-21.

The invention claimed is:

1. A method for treating cancer in a subject, comprising the step of administrating simultaneously, separately or sequentially to said subject a therapeutically amount of (i) a histone deacetylase inhibitor (HDACi) and (ii) a vaccine composition containing a population of pluripotent cells that have been inactivated.

2. The method of claim 1, further comprising the step of administering an HDACi for a period of time after the administration of the vaccine composition.

3. The method of claim 1, wherein the cancer is selected from liver cancer, bladder carcinoma, breast carcinoma, cervical carcinoma, cholangiocarcinoma, colorectal carcinoma, gastric sarcoma, glioma, lung carcinoma, lymphoma, acute and chronic lymphoid and myeloid leukemias, melanoma, multiple myeloma, osteosarcoma, ovarian carcinoma, pancreatic carcinoma, prostate carcinoma, stomach carcinoma, kidney carcinoma, a head and neck tumor, and a solid tumor.

4. The method of claim 1, further comprising performing one or more of radiation therapy, targeted therapy, immunotherapy, or chemotherapy to the subject.

5. The method of claim 1, wherein the pluripotent cells are selected from human embryonic stem cells, induced pluripotent stem cells (iPS), allogeneic stem cells, xenogeneic stem cells, autologous stem cells and syngeneic stem cells.

6. The method of claim 1, wherein the administration of the pluripotent cells is performed by intradermal, intravenous, subcutaneous, or intramuscular injection.

* * * * *